United States Patent
Tsang

[19]

[11] Patent Number: 6,032,313
[45] Date of Patent: Mar. 7, 2000

[54] HOUSEHOLD APPLIANCE HAVING PLURAL COAXIALLY ROTATABLE OR PARALLEL LINEARLY MOVABLE HEADS OR TOOLS

[76] Inventor: Koon Keung Tsang, Flat X, 9th Floor, Valient Industrial Centre, 2-12 Au Pui Wan Street, Shatin, The Hong Kong Special Administrative Region of the People's Republic of China

[21] Appl. No.: 08/852,000

[22] Filed: May 6, 1997

Related U.S. Application Data

[63] Continuation-in-part of application No. 08/452,100, May 26, 1995, abandoned.

[30] Foreign Application Priority Data

May 24, 1996 [EP] European Pat. Off. ............. 96303731

[51] Int. Cl.[7] ........................... A46B 13/02; A47L 11/00; A47L 23/00; A61H 15/00
[52] U.S. Cl. ............................ 15/22.1; 15/22.2; 15/22.3; 15/28; 15/21.1; 15/97.1; 15/97.2; 15/30; 15/34; 15/36; 601/122; 601/123; 451/259; 451/343; 451/359
[58] Field of Search ..................................... 15/22.3, 22.1, 15/22.2, 28, 29, 49.1, 97.1, 97.2, 97.3, 21.1, 30, 32, 34, 33, 36; 601/112, 118, 119, 122, 123, 126; 451/259, 343, 359

[56] References Cited

U.S. PATENT DOCUMENTS

| | | | |
|---|---|---|---|
| 1,796,641 | 3/1931 | Zimmerman | 15/29 |
| 2,728,928 | 1/1956 | Beeren | 15/29 |
| 4,856,133 | 8/1989 | Sanchez | 15/29 |
| 5,007,127 | 4/1991 | Paolo | 15/29 |
| 5,337,435 | 8/1994 | Krasner | 15/28 |
| 5,353,460 | 10/1994 | Bauman | 15/22.1 |
| 5,354,246 | 10/1994 | Gotman | . |
| 5,355,638 | 10/1994 | Hoffman | . |
| 5,358,328 | 10/1994 | Inoue | . |
| 5,416,942 | 5/1995 | Baldacci | 15/22.1 |
| 5,619,766 | 4/1997 | Zhadanov | 15/29 |

FOREIGN PATENT DOCUMENTS

| | | | |
|---|---|---|---|
| 324221 | 5/1970 | Finland | 15/22.1 |
| 3512190 | 10/1986 | Germany | 451/359 |
| 2175494 | 12/1986 | United Kingdom | 15/29 |
| 91 13570 | 9/1991 | WIPO | 15/22.1 |
| 94 26144 | 11/1994 | WIPO | 15/29 |

*Primary Examiner*—Randall E. Chin
*Attorney, Agent, or Firm*—Bacon & Thomas

[57] ABSTRACT

A household appliance of the type in which a cleaning, polishing, or massaging effect is obtained by a rotating head or tool is improved by splitting the cleaning, polishing, or massaging head or tool into concentric or parallel multiple heads or tools arranged for coaxial or side-by-side differential motion.

29 Claims, 31 Drawing Sheets

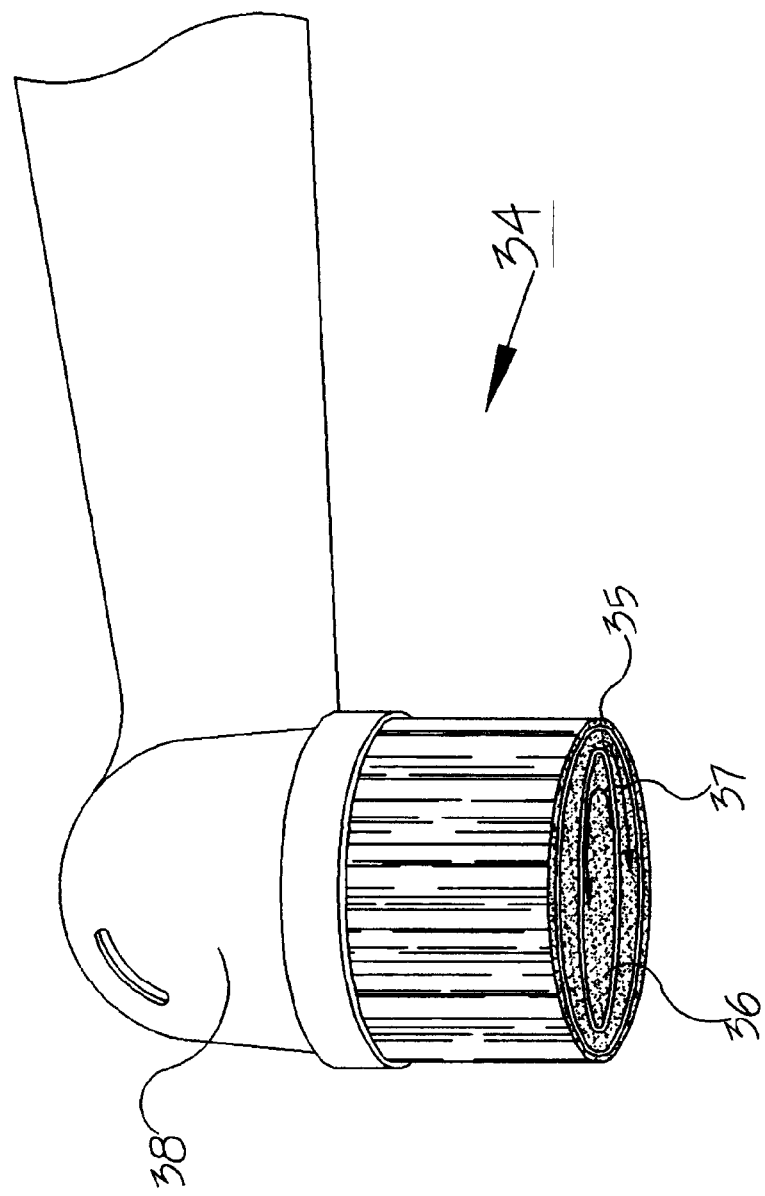

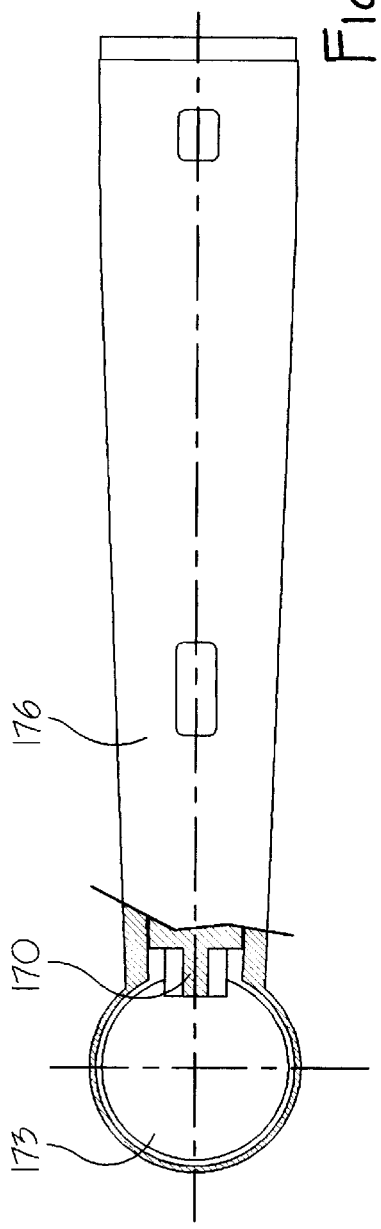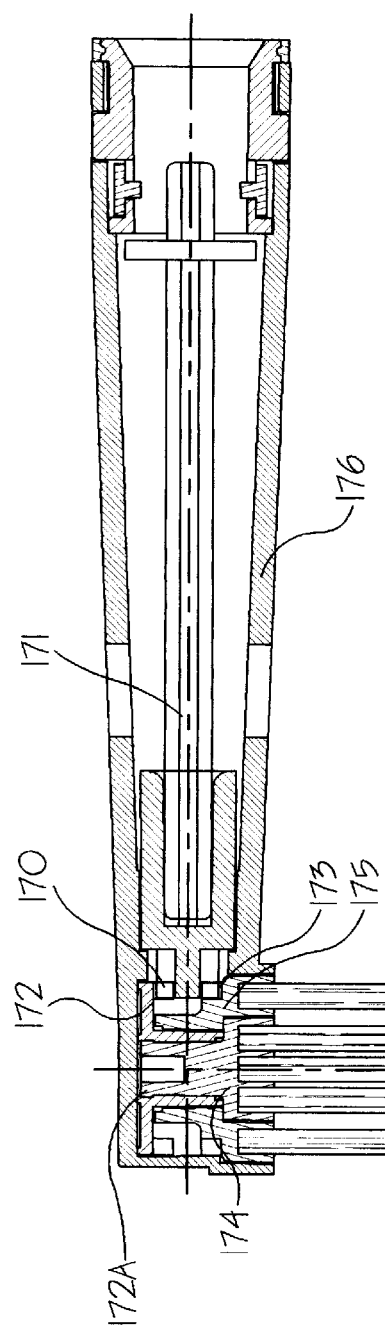

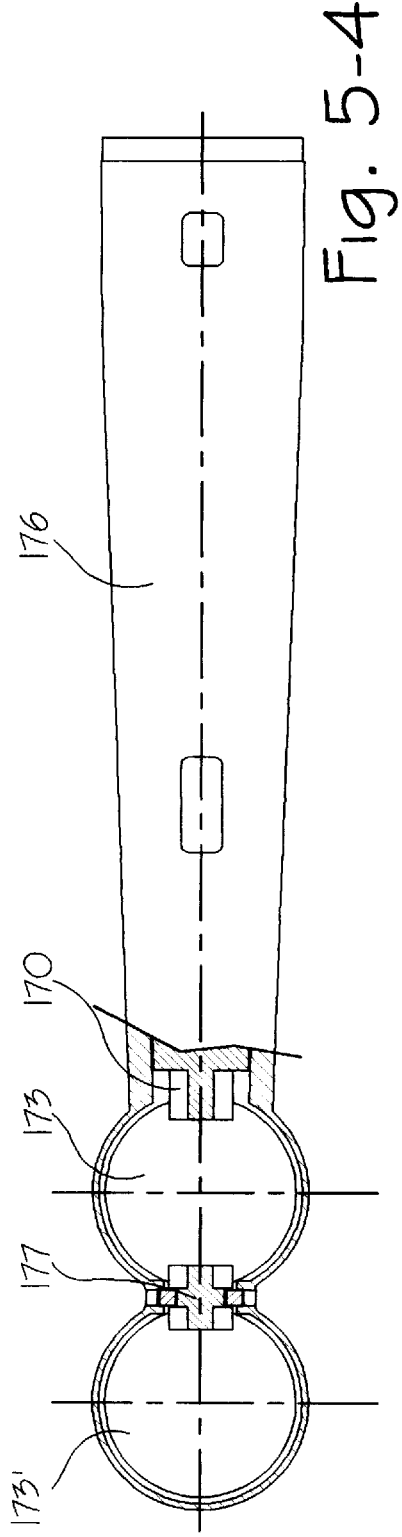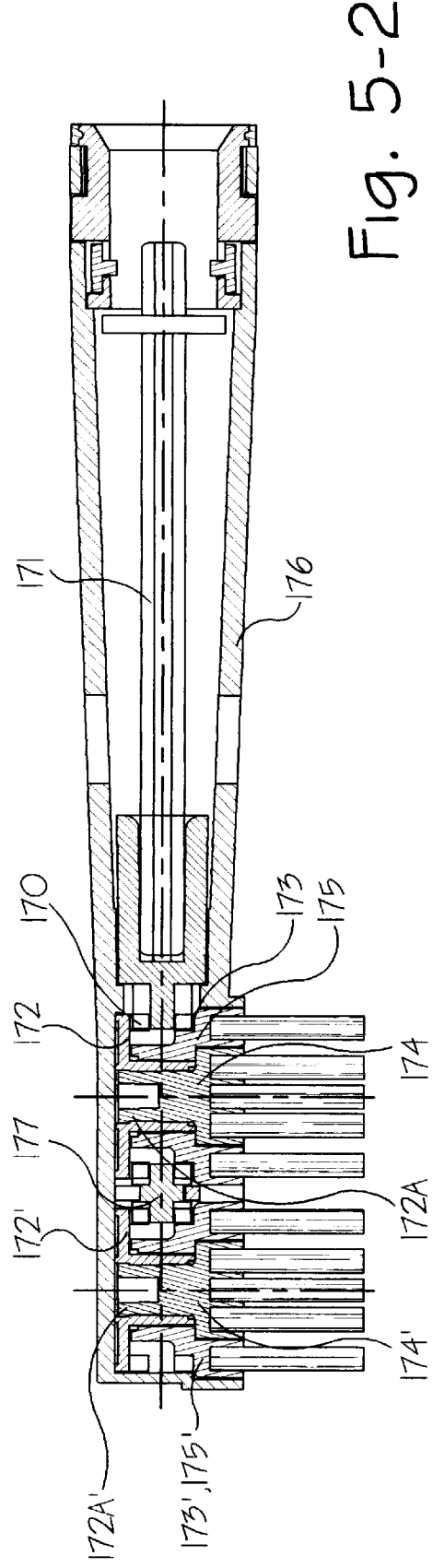

HOUSEHOLD APPLIANCE HAVING PLURAL COAXIALLY ROTATABLE OR PARALLEL LINEARLY MOVABLE HEADS OR TOOLS

CROSS-REFERENCE TO RELATED APPLICATION

This application is a Continuation-In-Part of patent application Ser. No. 08/452,100, filed May 26, 1995, now abandoned.

BACKGROUND OF THE INVENTION

1. Field of the Invention

This invention relates to a household appliance having rotating or reciprocating heads, such as a rotating or reciprocating cleaning brush, electric toothbrush, massager, or polisher.

2. Description of Related Art

The household appliances with which the present invention is concerned normally consist of a head or tool attached to directly to a shaft so as to rotate or oscillate therewith, in order to provide some sort of cleaning, brushing, polishing, or massaging effect.

While it would appear to be difficult to improve upon the brushing, cleaning, polishing, or massaging effect of these conventional household appliances, the inventor has discovered several disadvantages which are solved by the present invention. The disadvantages are 1.) that any rotating device which is pressed against a surface to carry out its function will generate a counter-torque which increases with the power of the device, making the device difficult to handle, 2.) when the surface is uneven, for example at a corner, the device will move erratically due to the lack of symmetry in the motion of the device, 3.) in the case of a cleaning device, debris loosened by the cleaning device will tend to be pressed into the surface rather than removed, and 4.) in the case of a brush having relative long bristles arranged to extend into holes or crevices, for example if the bristles are longer than the circumference diameter of the outer ring of bristles, the bristles will tend to twist in one direction reducing the contact area of the bristles against surfaces of the hole or crevice, as shown in FIG. 21.

The present invention is intended to increase the efficiency of such devices, by splitting the head or tool by which the function of the device is carried out into multiple heads or tools having a differential motion. This has the advantages of 1.) offsetting or canceling out the counter-torque effect, thereby making the device easier to handle, 2.) generally balancing the forces applied by the device to permit the device to be used on uneven surfaces, edges, and corners, 3.) providing a cross-cleaning effect at the point where the different sections of the device move in different directions or at different speeds, and reducing bristle twisting effect in the case of a brush.

The solution to the problem of counter-torque in a multiple head or tool device depends, as those skilled in the art might expect once the concept of multiple rotating heads or tools is understood, on the masses and angular velocities of the rotating heads or tools, with the counter-torque being minimized if the masses and velocities are such that the vector sum of the contributions from each of the individual heads or tools to the overall or net torque is zero. In addition, however, the inventor has found that the contact areas and materials of the contact surfaces of the various heads or tools, which contribute to the dynamic friction coefficients of the contact surfaces, also contribute significantly to the net torque, and must be taken into account in order to minimize the counter-torque.

On the other hand, while elimination of counter-torque can be accomplished by any tool or head configuration in which the torques on individual heads or tools are caused to balance out or substantially add to zero, in the case of cleaning heads of tools such as brushes cross-cleaning is most intense when adjacent heads are rotated such that the linear velocities (v) of respective points on relatively moving adjacent edges of the heads have equal magnitudes and opposite directions. This occurs when the "angular velocity" of each pair of adjacent counter-rotating heads has an equal magnitude (angular speed) and opposite direction, with the number of heads (and the width of the layers) determining the number of interfaces at which cross-cleaning effects are most intense.

FIGS. 1-1 and 1-2 illustrate the relationship between "linear speed" and radius in a two layer counter-rotating brush assembly in which the counter-rotating brushes have the same angular speeds, while FIGS. 1-3 and 1-4 illustrate the relationship between "linear speed" and radius in a four layer counter-rotating brush assembly, and FIGS. 1-5 and 1-6 illustrate the relationship in an eight layer assembly. As is apparent from these Figures, the linear speed, which is the relative instantaneous speed between a bristle and the portion of the surface which is being contacted by the bristle, increases linearly across each of the brush heads while at the interface between brush heads, the linear speed of respectively adjacent bristles on the heads is exactly the same but opposite in direction.

Because cross-cleaning occurs between adjacent heads, improved cross-cleaning is obtained with each head added. In addition, as the number of heads increases, and the torque variations across the radii of the heads decreases, the balancing effect also improves, with perfect balance being achieved in theory by an infinite number of heads with infinitesimally small differences in radii across the heads (referred to as the infinitesimal balancing effect). While cost of construction will eventually limit the number of heads, the invention in theory enables cross-cleaning and balancing to be made as close to optimum as desired by increasing the number of heads.

It is known, of course, to provide small appliances such as electric toothbrushes with multiple heads or tools mounted on parallel shafts to rotate in opposite directions. While such appliances are in widespread usage, however, the use of completely separate heads or tools mounted on separate shafts does not optimize the cleaning to any significant degree, but rather simply increases the coverage of the device in order to reduce cleaning time. In contrast, the present invention seeks to split a single tool or head into multiple heads or tools with differential movement not to increase the area cover during one pass of the device, but to provide a variety of performance improvements, including increasing the intensity of the effect provided by the multiple heads in comparison with a conventional rotating or reciprocating device of like area.

While counter-rotating head devices have been proposed for certain specialized applications, such as the spotting brush of U.S. Pat. No. 1,796,641, the counter-rotation taught by the prior art is not such as is necessary to obtain a cross-cleaning effect or to provide a balancing counter-torque (to the contrary, the torque resulting from the spotting action in the '641 patent appears to be de minimus). In addition, although it is known to provide a toothbrush with oscillating counter-rotation as described in U.S. Pat. No.

5,416,942, the prior art fails to recognize the advantages of cross-cleaning by one-way counter-rotation of each head, much less the generalized principles of counter-rotation or side-by-side oscillation discovered by the present inventor which would have made the applicability of the invention to other types of devices evident to the ordinary artisan.

The splitting of a single head or tool into concentric or parallel multiple heads or tools arranged for coaxial rotation or side-by-side oscillation according to the present invention not only solves the above-mentioned problems of conventional devices, but also does so without significantly increasing the complexity of the device, since according to preferred embodiments of the invention, a single drive shaft can be used (although the use of a single drive shaft is not necessary to the invention in its broadest form, since the advantages of easier handling and improved cleaning do not depend on the specific mechanical arrangement used to achieve the differential rotation effect).

The advantage of eliminating counter-torque increases with the power of the device. If one presses a small conventional rotating brush against a surface, there will be a small torque in the direction opposite the direction of rotation, which is countered by the force of the person holding the brush, and which may not even be felt by that person. As power increases, however, a point is eventually reached where it will become impossible to hold the brush. By bifurcating the brush motion into two oppositely rotating sections, the problem of counter-torque will clearly be minimized even for very high power devices which could not ordinarily be handled by the average user. The balancing problem is especially apparent in devices intended to be used on uneven surfaces, such as a car polisher, and also in devices such as floor buffers which have an odd number of heads, and therefore an inherently unbalanced torque.

The cross-cleaning advantage applies even in the case of ordinary linearly reciprocating electric toothbrushes, which one would expect to remove dirt effectively despite the lack of differential motion due to the reversal of motion at the ends of the oscillations. The problem is that either the amplitude of the oscillations is so small that the cleaning tip of the soft bristles will remain relatively stationary even as the brush head moves, or the amplitude will be sufficiently large that the brush head will have moved to another surface before it reverses direction, greatly reducing the cross-cleaning effect provided by the reversal of motion at the end of the oscillations.

While the general concept of providing concentric or parallel multiple heads or tools arranged for coaxial rotation or side-by-side oscillation is believed to be novel and non-obvious, in the intended context of small household appliances, and in particular the cleaning and personal grooming devices described below, those skilled in the art will recognize that the specific mechanical arrangements utilized to achieve the desired differential motion may be in the form of gearing or transmission arrangements which are per se known, although not in the specific context disclosed. The use of bevel gears and planetary or ring/idler gear combinations is of course known and thus the invention in general is not intended to be limited to any such arrangements, although some of the mechanical expedients used to implement the present invention are believed to be especially advantageous in terms of efficiency, reliability, and cost, and thus form a proper basis for one or more claims.

SUMMARY OF THE INVENTION

It is accordingly a first objective of the invention to provide a household appliance having concentric multiple heads or tools driven to rotate or move linearly in an oscillating or continuous motion, at different respective speeds and/or in different directions, and to achieve such motions with especially efficient mechanical constructions, including modular constructions which provide for easy servicing or replacement of the counter-rotating head assemblies.

It is a second objective of the invention to provide a household appliance having concentric multiple heads or tools driven to rotate or move linearly in an oscillating or continuous motion, at different respective speeds and/or in different directions, thereby providing a counter-torque so as minimize the effort needed to utilize the device, improve balance, and, in the case of a cleaning head or brush, assist in the removal of loosened debris and reduce the twisting effect on relatively long bristles.

It is a third objective of the invention to provide a rotating cleaning brush made up of concentric multiple bristle assemblies arranged to rotate coaxially at different velocities and/or in different directions, and in particular to provide a rotating brush made up of two or more concentric bristle assemblies which rotate coaxially in opposite directions.

It is a fourth objective of the invention to provide an electric toothbrush made up of concentric multiple bristle assemblies arranged to rotate coaxially at different velocities and/or in different directions, and in particular to provide an electric toothbrush which includes at least two concentric bristle assemblies which rotate coaxially in opposite directions.

It is a fifth objective of the invention to provide a polisher or buffer which includes concentric multiple polishing head assemblies arranged to rotate coaxially at different velocities and/or in different directions, and in particular to provide a car, shoe, or floor polisher which includes two concentric polishing head assemblies which rotate coaxially in opposite directions.

It is a sixth objective of the invention to provide a massager which includes concentric multiple massage head assemblies arranged to rotate coaxially at different velocities and/or in different directions, and in particular to provide a massager which includes two concentric massage head assemblies which rotate coaxially in opposite directions.

It is a seventh objective of the invention to provide a linearly reciprocating brush made up of generally parallel multiple bristle assemblies arranged to move at different velocities and/or in different directions, and in particular to provide a linearly reciprocating cascade brush made up of at least two bristle assemblies which move in opposite directions.

It is an eighth objective of the invention to provide a linearly reciprocating massager made up of parallel multiple massage heads arranged to move at different velocities and/or in different directions, and in particular to provide a linearly reciprocating massager made up of at least two massage heads which move in opposite directions.

It is a ninth objective of the invention to provide a fingernail cleaning device made up of coaxial brush assemblies arranged to rotate at different velocities and/or in different directions, and in particular to provide a fingernail cleaner which includes two coaxial fingernail cleaner head assemblies which rotate coaxially in opposite directions.

It is a tenth objective of the invention to provide a rotating brush having relatively long bristles but in which bristle twisting effects are minimized.

BRIEF DESCRIPTION OF THE DRAWINGS

FIGS. 1-1 to 1-6 are schematic diagrams illustrating further principles of the invention.

FIG. 2 is a cross-sectional side view of a cleaning brush design constructed in accordance with the principles of the first preferred embodiment of the invention.

FIG. 2-1 is a cross-sectional side view of a variation of the brush design illustrated in FIG. 2.

FIG. 2-2 is a side view of the brush design illustrated in FIG. 2-1.

FIG. 2-3 is a cross-sectional side view of a variation of the brush design illustrated in FIGS. 2-1 and 2-2.

FIG. 2-4 is a bottom view of the brush design variation illustrated in FIG. 2-3.

FIG. 3 is an end view of the cleaning brush design of FIG. 2.

FIG. 4 is a cross-sectional side view of a counter-rotating toothbrush head design constructed in accordance with the principles of the first preferred embodiment of the invention.

FIGS. 5, 5-1, and 5-2 are perspective views of variations of the counter-rotating toothbrush head design illustrated in FIG. 4.

FIGS. 5-3 and 5-4 are respective top views of the toothbrush designs illustrated in FIGS. 5-1 and 5-2.

FIG. 6 is a cross-sectional side view of a three-dimensional variation of the cleaning brush design of FIGS. 2 and 3.

FIGS. 20-1 and 20-2 are cross-sectional views showing the manner in which the cleaner of FIG. 20 is utilized.

FIG. 20-3 is a plan view of the cleaner of FIG. 20.

DETAILED DESCRIPTION OF THE PREFERRED EMBODIMENTS

Figure 1:
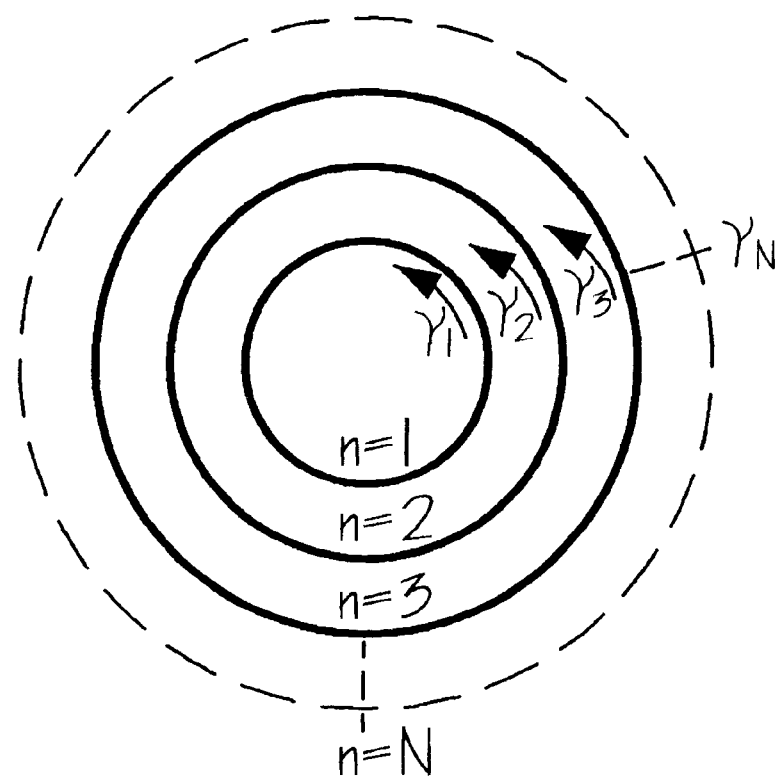
FIG. 1 is a schematic diagram illustrating the principles of a household appliance having a tool or head made up of coaxial differentially rotatable assemblies according to a first preferred embodiment of the invention.

As illustrated in FIG. 1, the first preferred embodiment of the invention provides an appliance having a rotating head or tool made up of concentric rotating discs and annular members each capable of rotating at a speed $v_n$, where $n=1,2,3,4, \ldots ,N$. The speed $v_n$ can be positive, negative (i.e., the reverse direction of positive), or zero (i.e., stationary). In most of the illustrated applications of this embodiment of the invention, except for the embodiment shown in FIG. 5, $n=2$, $v_1=+ve$, and $v_2=-ve$, but it will be appreciated by those skilled in the art that n, $v_1$, and $v_2$ may be varied depending on the application, and the degree to which the various advantages of the invention are to be achieved.

In particular, for devices in which counter-torque is to be minimized by balancing the torques on individual rotating assemblies, so that vector sum of the torques is approximately zero, the number of assemblies or sections the speeds and directions of individual assemblies or sections may be freely varied so long as the sum of the torques for all of the assemblies approaches the desired level. Since the torques on individual assemblies or sections depends also on the contact areas and materials of the contact surfaces, these factors must be taken into account when selecting the speeds and directions of the individual assemblies. Of course, where the materials of the contacts surfaces are uniform across the device, only the velocities (speed and direction) and the contact areas need generally be taken into account, although there might be some cases in which non-linear dynamic coefficients of friction for certain materials might have an effect on the torque calculations.

On the other hand, in the case of a cleaning device, where the cross-cleaning effect of counter-rotating devices is to be maximized, the preferred configuration is as discussed above to rotate adjacent assemblies in opposite directions at substantially the same angular speed, so that the linear speed at the boundaries between assemblies is approximately the same, and to increase the number of assemblies with the overall diameter or area of the contact surface to maximize the number or locations at which cross-cleaning can occur. In addition, where the assemblies are all rotating in opposite directions at generally the same speed, balancing will be improved for larger diameter contact surfaces if the number of assemblies or sections is increased, i.e., if the number "n" of layers is increased.

Figure 11:
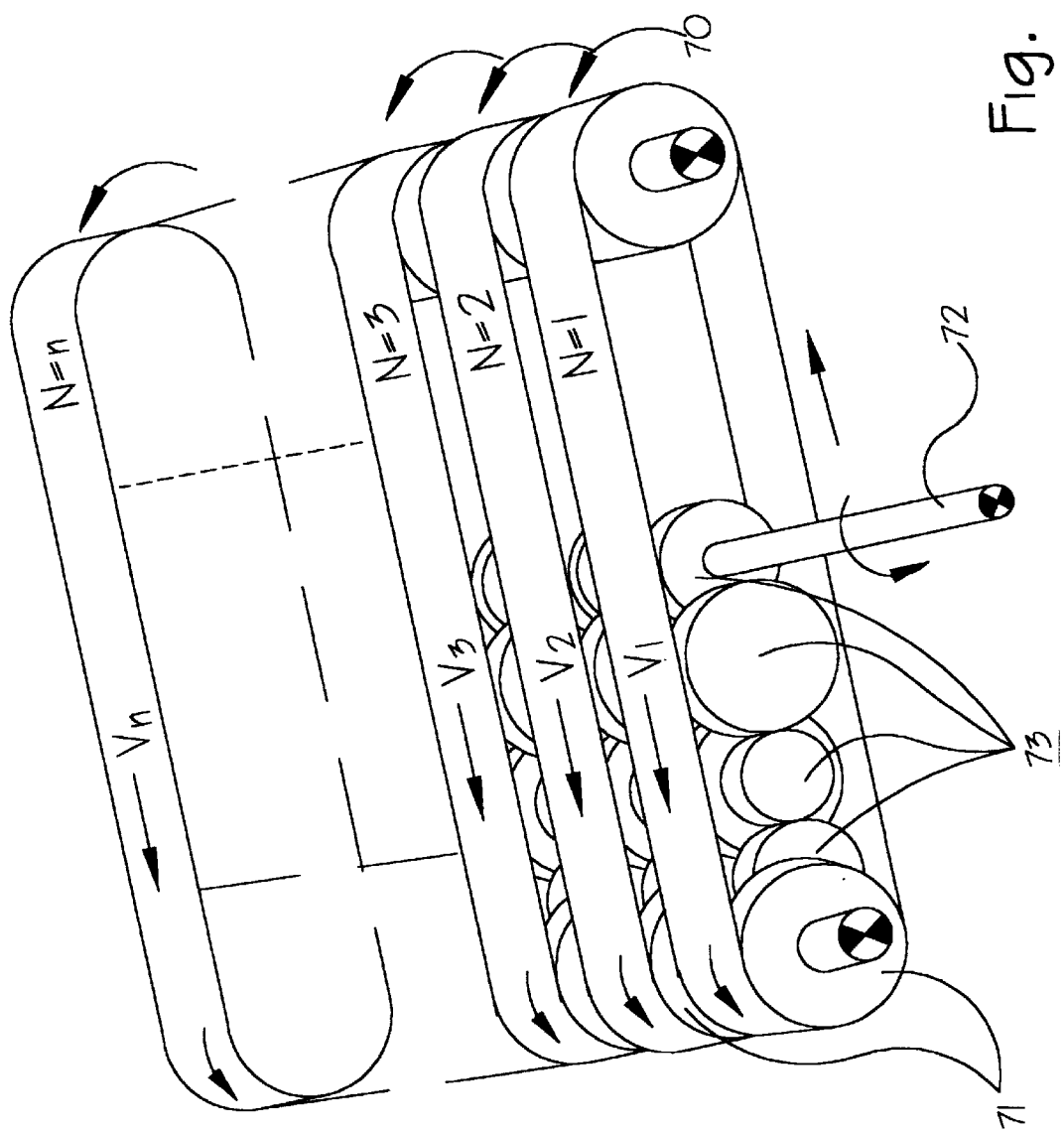
FIG. 11 is perspective view illustrating an arrangement for providing linear movement at different velocities of a plurality of tools or heads arranged in side-by-side fashion according to a second preferred embodiment of the invention.
Figure 15:
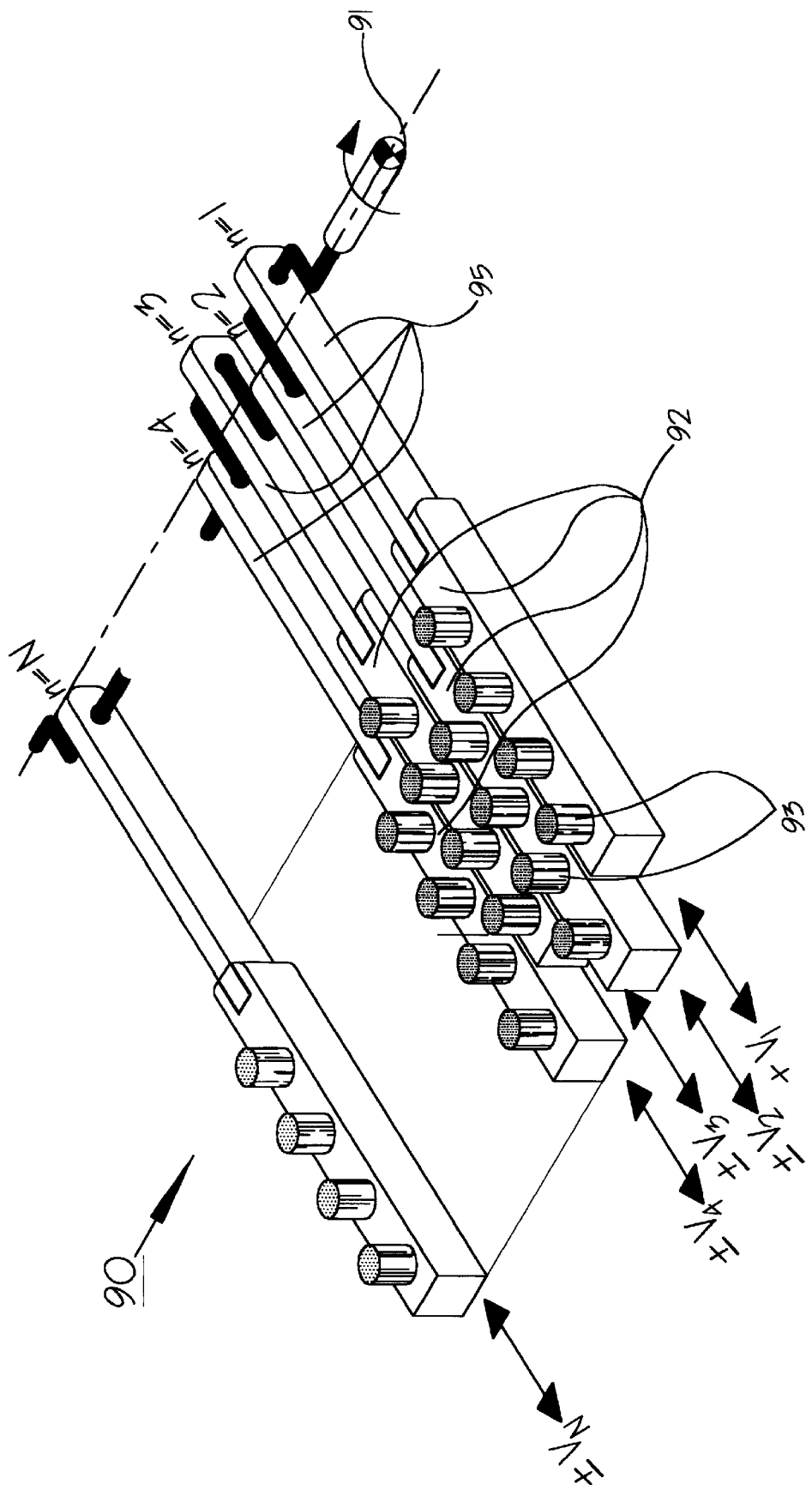
FIG. 15 is a perspective view illustrating an arrangement for providing linear movement in opposite directions of a plurality of tools or heads arranged in side-by-side fashion according to another preferred embodiment of the invention.

Thus, within the scope of the invention, the appliance may have a head or tool split into three or more assemblies or sections which all rotate coaxially but at different speeds and in the same or different directions. In addition, the directions of any individual assembly may be reversed periodically by an electrical or mechanical switching arrangement so that rather than rotating continuously, the individual assemblies may rotate back and forth, and by extending the principles of the first preferred embodiment to "rotating" assemblies in which the radius is infinitely large, one can provide individual assemblies which move linearly in either different directions or at different velocities, as generally illustrated in FIGS. 11 and 15, discussed in more detail below.

Figures 1, 2:
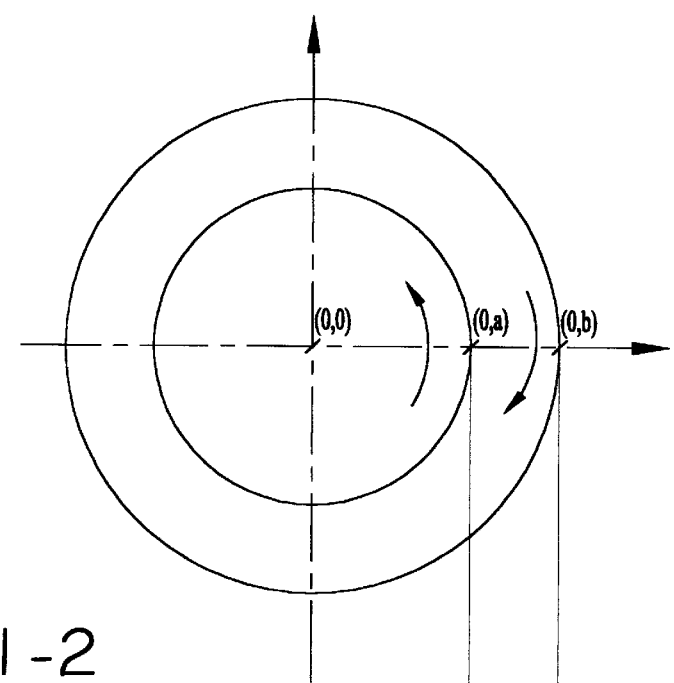
Figure 1:
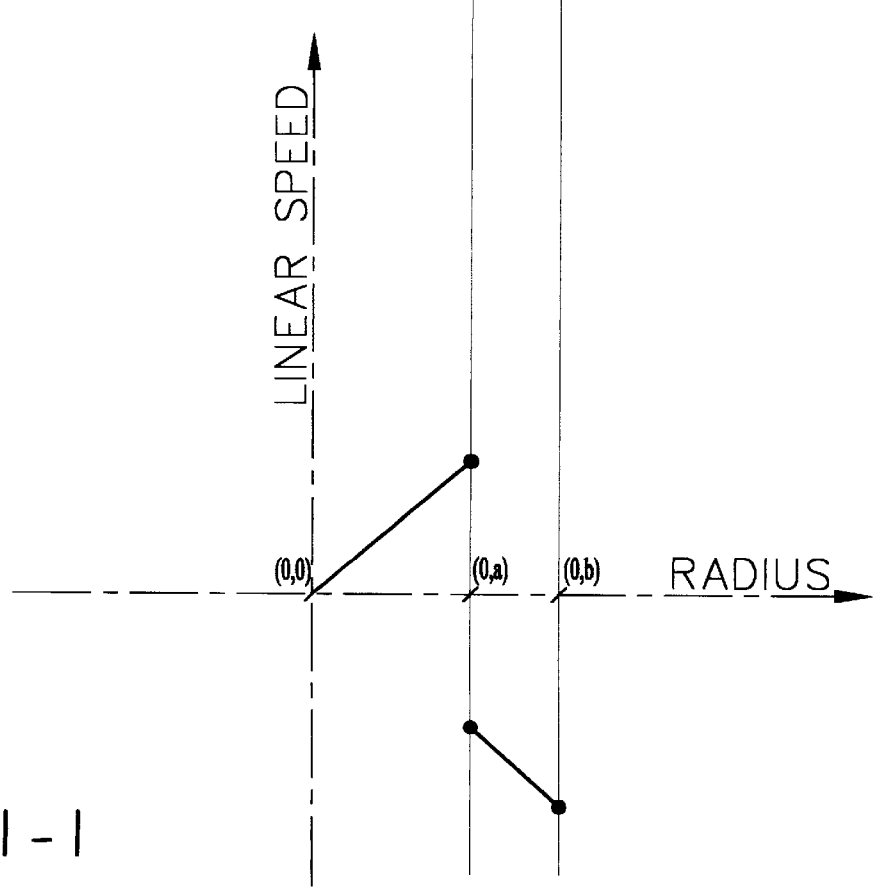
Figures 1, 2, 3, 4:
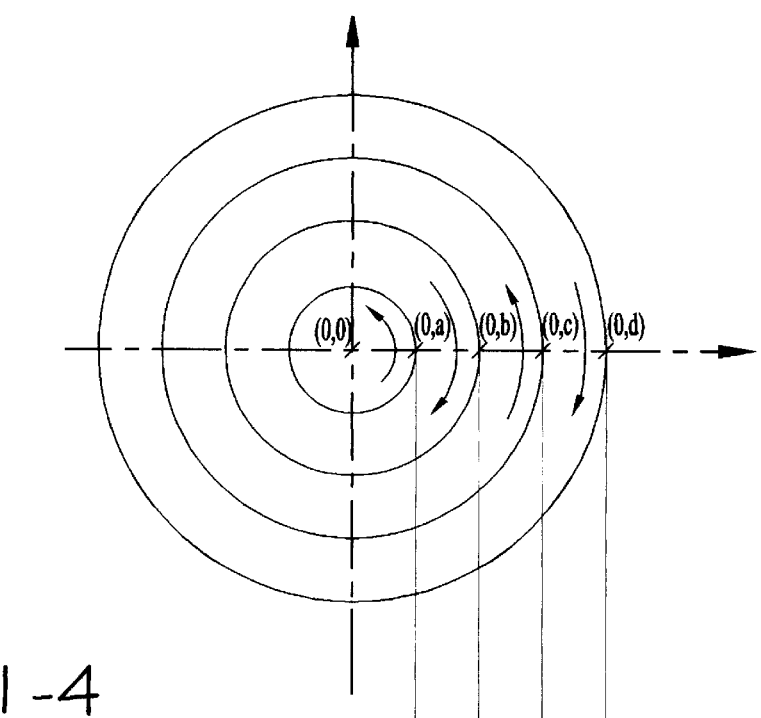
Figures 1, 2, 3:
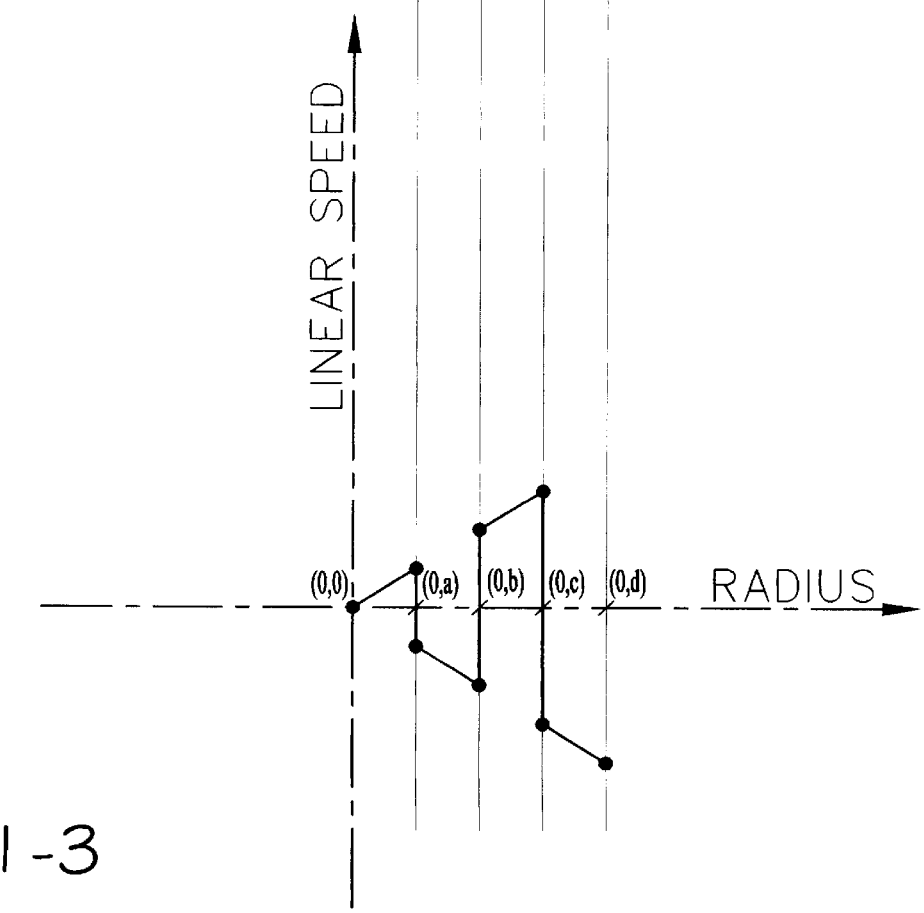

FIGS. 2, 2-1, and 3 show a first example of the above principles, in which the household appliance having a rotating head is a cleaning brush 1. In these examples, the power input is provided by a rotating shaft 2 or equivalent rotating shaft 151 driven by a motor (not shown). Those skilled in the art will appreciate that any motor can be used, and that details of the motor form no part of the invention.

Turning specifically to the variation shown in FIG. 2, shaft 2 is supported by appropriate bearings in a housing 3, to which is affixed bearing members 4–7, bearing member 4 being preferably affixed to housing 3 by an additional sleeve 6'. Both shaft 2 and an outer bristle supporting member 8 are rotatable relative to bearing members 4–7.

The brush assembly of the counter-rotatable cleaning brush of this variation of the first preferred embodiment of the invention includes an inner circular bristle 9 and an outer annular bristle assembly 10 arranged to rotate in opposite directions and supported, respectively, by cylindrical support member 11 and the above-mentioned support member 8. Support member 11 is preferably directly affixed to and rotated by shaft 2, while the counter-rotation effect for support member 8 and the second bristle assembly 10 is provided by a planetary gear system made up of a drive gear 12 affixed to the motor shaft 2, a ring gear 13 affixed to support member 8, and at least one idler gear 14 rotatable about a pin 15 secured to the bearing members 4–6 so as to prevent the idler gears 14 from revolving around the drive gear 12.

As a result of this structure, a brush is provided in which the outside bristles rotate in a direction opposite that of the inside bristles, thus providing an improved brushing effect without the need for a second motor or additional main shaft, or for significant modifications of the existing motor, drive shaft, and housing structure (although the improved brushing effect could also be achieved even if a second motor and/or shaft are provided). The only additions to the conventional structure which are required are a ring gear, idler gears, a drive gear on the shaft, and an additional support member for the outer bristle assembly.

In an especially efficient variation of the structure shown in FIG. 2, as illustrated in FIG. 2-1, the single ring and idler gear mechanism is replaced by a double ring gear mechanism made up of a first ring gear 150 driven by and secured to motor-driven shaft 151 to rotate therewith, at least one pinion 152, 153 rotatably connected to reversing brush module housing 154 by a pin 155,156 and bushing 157,158 and in engagement with first ring gear 150 to rotate in response to rotation of the first ring gear, and a second ring gear 159 rotatable relative to shaft 151 in a direction opposite the direction of rotation of the first ring gear 150 in response to rotation of the at least one pinion 155,156.

Because the inner and outer assemblies in this variation of the first preferred embodiment rotate in opposite directions at the same speed, the cross cleaning effect is optimized. Further, balancing is easily achieved by appropriate selection of the contact areas of the respective assemblies, taking into account the coefficients of the assemblies if the materials of the bristles between the inner and outer bristles is different, while both balancing and cross-cleaning can be improved, in this and the other variations of the illustrated embodiment, by increasing the number of rotating assemblies, i.e., by using a larger number n of layers.

In this variation of the preferred embodiment, the inner brush head 160 is affixed to the first ring gear 150 by means of a locking screw 161, with the first ring gear and inner brush head forming a bearing surface 162 for permitting counter-rotation relative to the second ring gear 159. In addition, the second ring gear is affixed to outer brush head 163 by, for example, location pins 164. As a result, the inner brush head 160 rotates with shaft 151 and outer brush head 163 rotates in an opposite direction relative to the shaft to obtain a counter-rotation effect for the respective inner bristles 165 and outer bristles 165'.

Attachment of the counter-rotating brush assembly to the motor unit is achieved by a sleeve 166 having latch arms 167 arranged to be inserted into and engage a central opening in a main housing 168 that contains the motor and gear trains required to drive shaft 151, thereby securing the brush assembly to the main housing as the shaft 151 is inserted or snapped into a bushing provided in the first ring gear 150.

In this design, sleeve 166 extends to form a cover for the brush head, with the cover portion 166' including openings for receiving locating splines 169 for orienting the brush head module thus formed with the main housing 168, resulting in a particularly convenient modular design which permits the brush head assembly to be easily removed for replacement or cleaning, as illustrated in FIG. 2-2. Of course, the modular design illustrated in FIG. 2-2 can be used with gear arrangements other than that shown in FIG. 2-1, including the gear arrangement shown in FIG. 2, as well as in other types of brushes employing the counter-rotation principles of the invention, and also in connection with the generalized form of the present invention in which there are n members and adjacent members rotate at different speeds and/or directions, as described above in connection with FIG. 1.

FIGS. 2-3 and 2-4 show a variation of the design shown in FIGS. 2-1 and 2-2, in which the number of brush heads is increased from two to four. Instead of the double ring gear mechanism of the embodiment shown in FIGS. 2-1 and 2-2, the mechanism of this embodiment is made up of first ring gear 250 driven by and secured to motor-driven shaft 251 to rotate therewith, idle gears 252–254 mounted for rotation by means of pins 256 secured in bushings 257 in the brush module housing 258 and engaged with respective brush units 259–262 such that idle gears 252 are rotated by ring gear 250, causing brush unit 260 to rotate at the same angular speed in an opposite direction to the direction of rotation of the ring gear, the rotation of brush unit 260 causing rotation of idle gears 253 and counter-rotation of brush unit 261, the counter-rotation of brush unit 261 causing rotation of idle gears 254 and rotation of brush unit 262. The first or inner brush unit 259 is directly connected to shaft 251 such that each adjacent brush unit rotates at the same angular speed and opposite direction.

Because the adjacent brush units in this embodiment rotate in opposite directions at the same speed, the cross cleaning effect is again obtained. Further, by increasing the number of brush units, balancing and cross-cleaning are improved according to the principles discussed above.

In this variation of the preferred embodiment, the inner brush unit 259 is affixed to ring gear 250 by means of a locking screw 264, with the inner brush unit including a bearing surface 265 for permitting relative rotation of the second brush unit 260, the second brush unit including a bearing surface 266 for the third brush unit 261, and the third brush unit including a bearing surface 267 for the fourth brush unit 262. Preferably, each of the brush units can be snap fit into the brush module housing 258.

Attachment of the brush module housing 258 to the motor unit may be achieved, in a manner similar to the embodiment of FIGS. 2-1 and 2-2, by a member 267 having latch arms 268 arranged to be inserted into and engage a central opening in a main housing 269 that contains the motor and gear trains required to drive shaft 251, thereby securing the brush assembly to the main housing as the shaft 251 is inserted or snapped into a bushing provided in the ring gear 250.

While the above embodiments of the invention are disclosed in a very specific manner, those skilled in the art will appreciate that the broadest concepts of the invention are applicable to numerous multiple rotating head arrangements other than the illustrated ones, including arrangements in which the heads of a particular device have different radii, materials, and even functions. By changing the gear ratios of the respective gears, e.g., by adding gears, a differential speed between inner and outer brushes moving in the same or opposite direction can also be obtained to meet the requirements of different applications and situations. In addition, the principles of the invention can also be adapted to different applications and situations by varying the total contact areas of the inner and outer bristles, and/or by axially offsetting the inner and outer differentially rotating members.

Figures 1, 2, 3, 4, 5, 6:
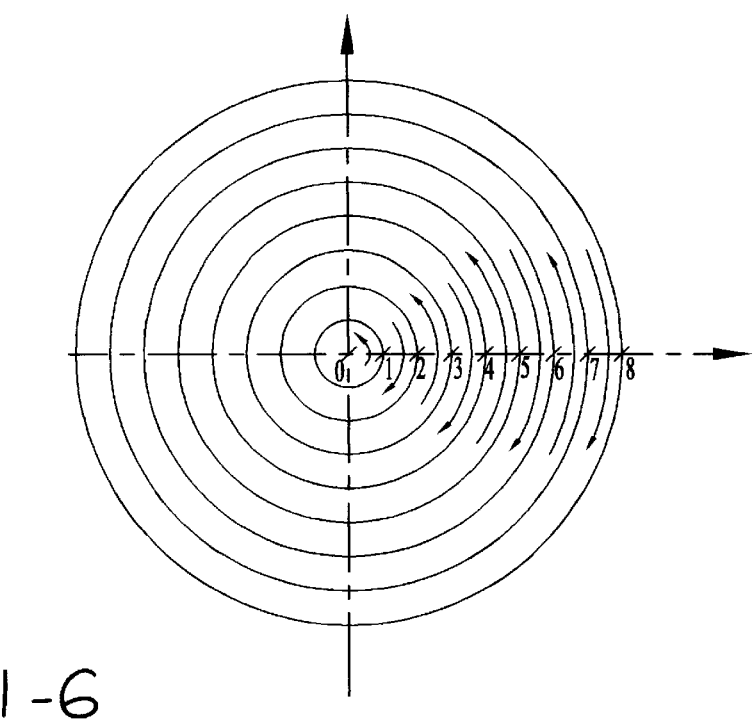
Figures 1, 2, 3, 4, 5:
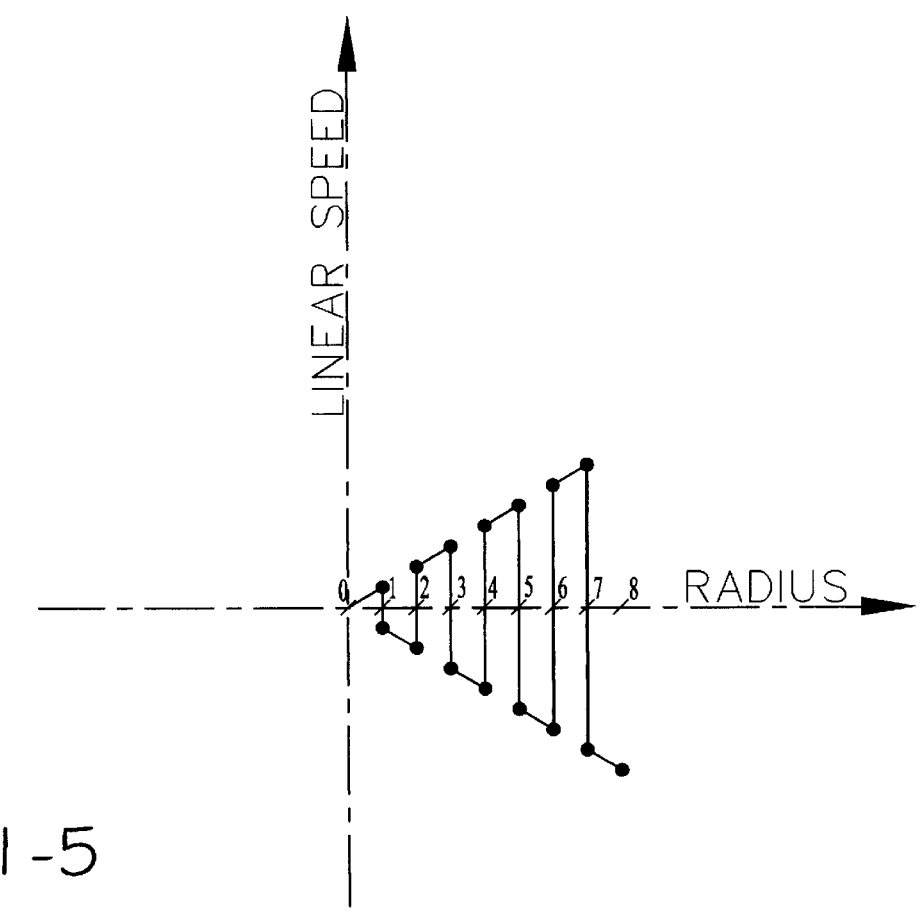
Figure 2:
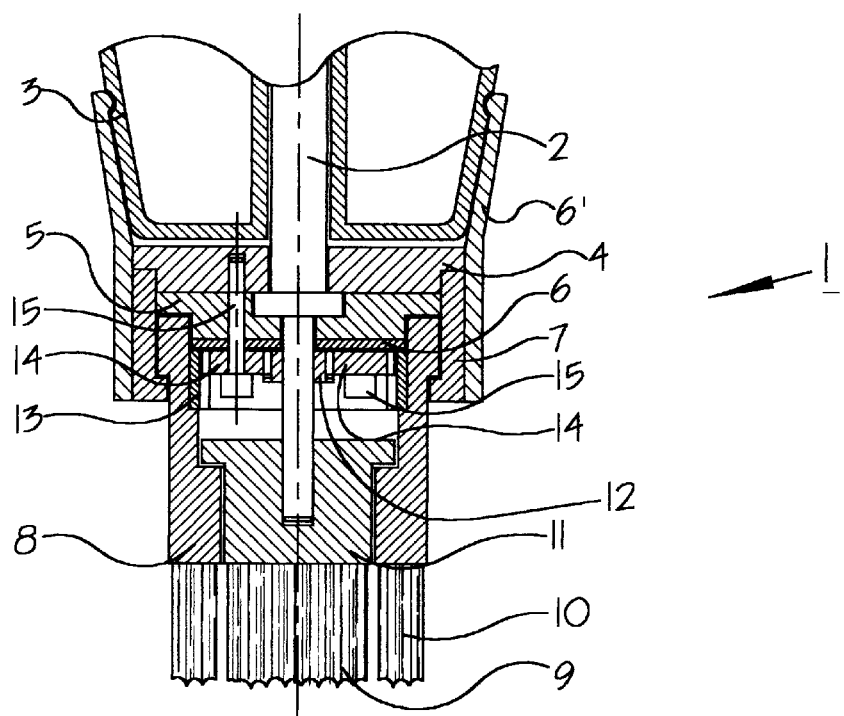
Figure 3:
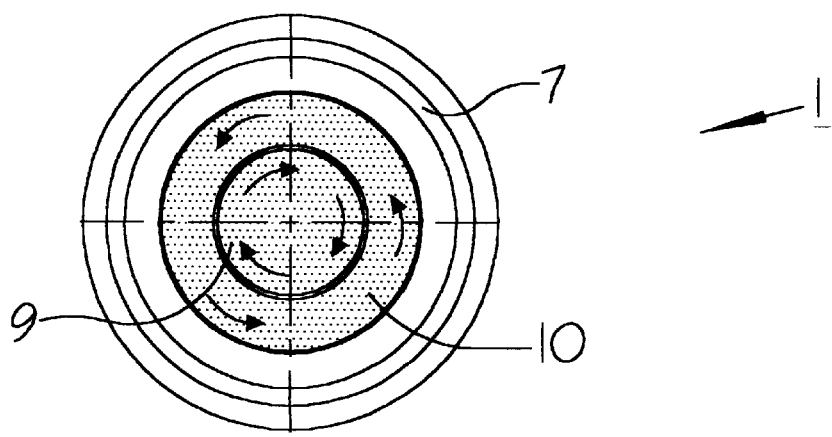
Figures 1, 2:
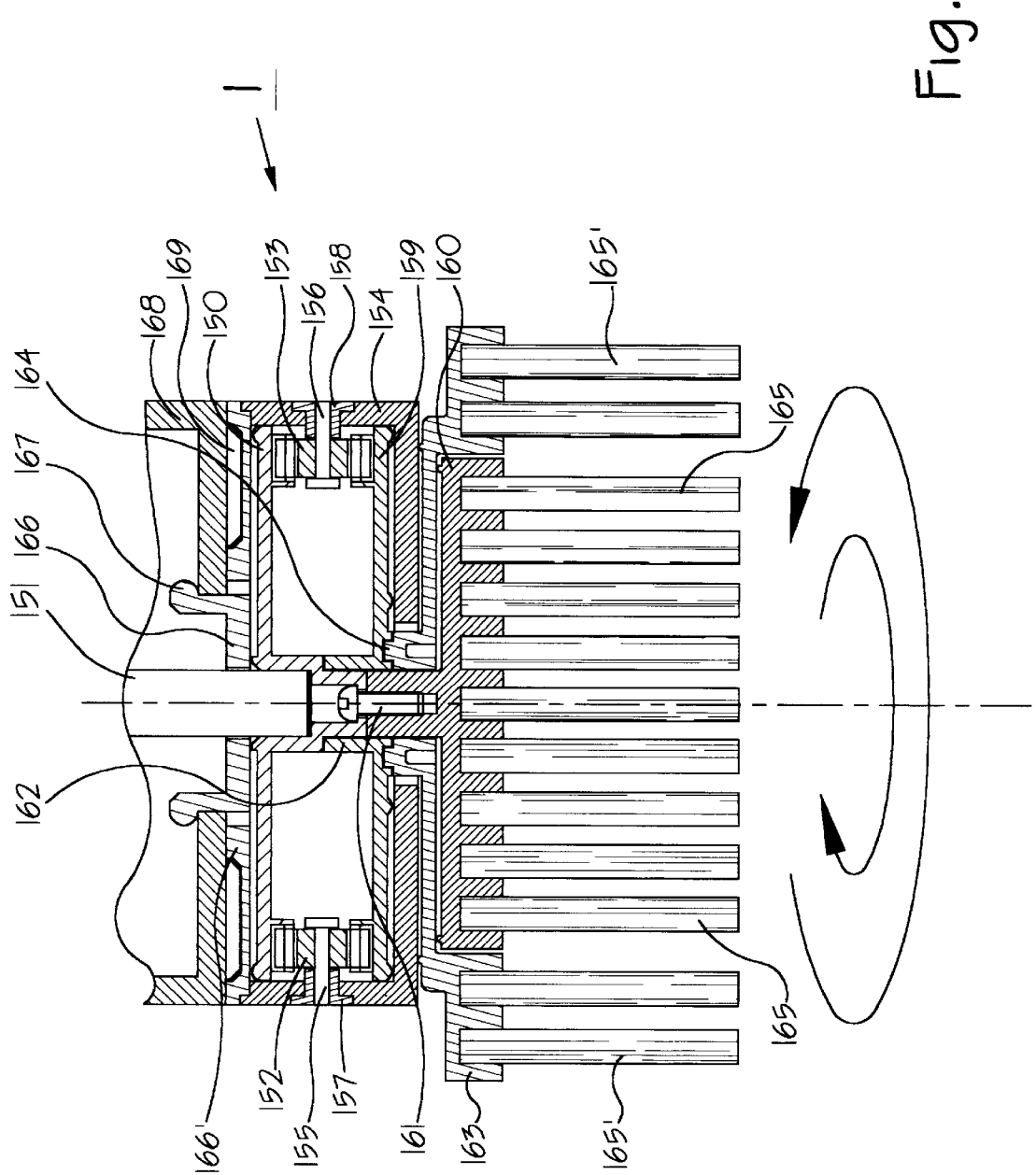
Figure 2:
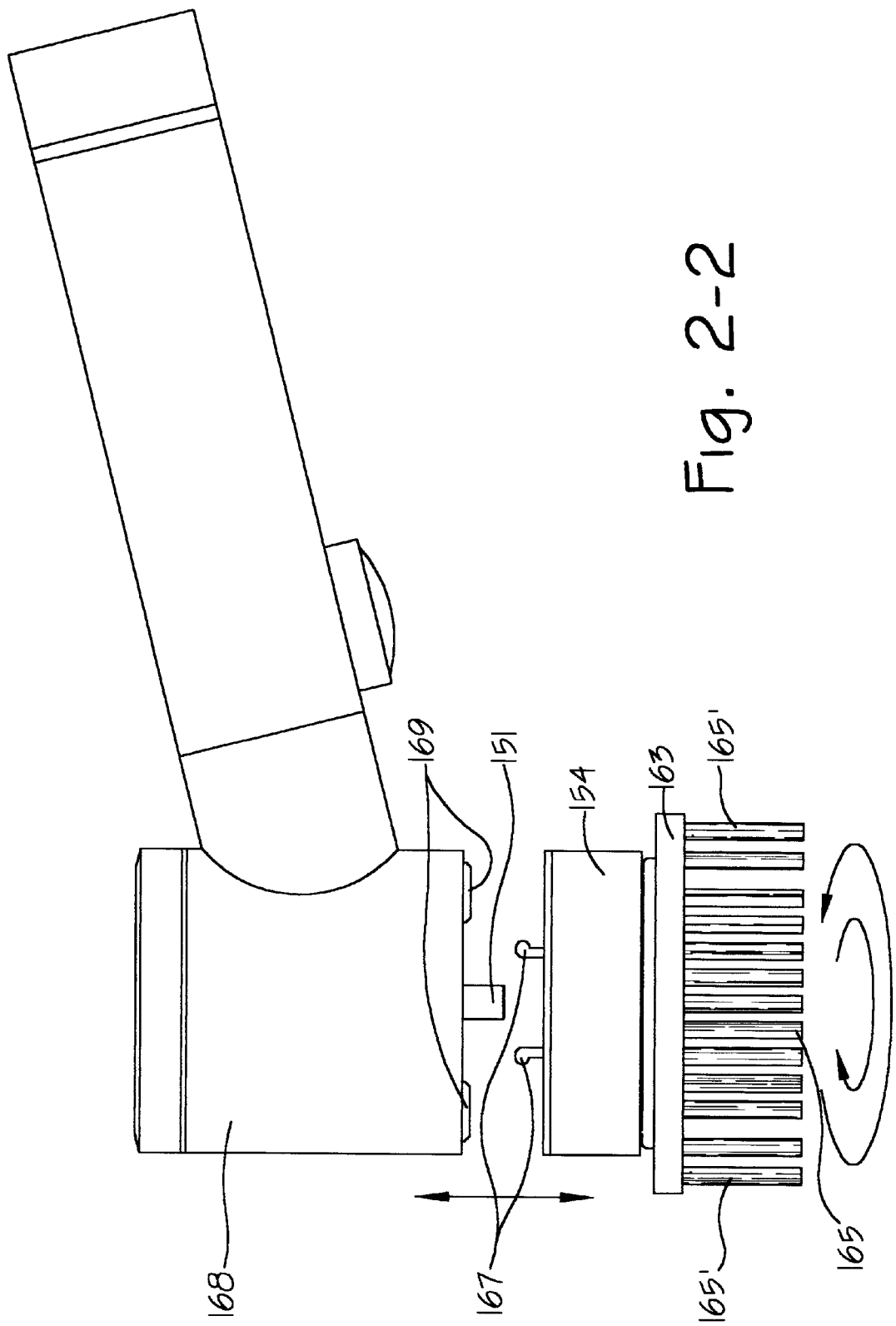
Figures 2, 3:
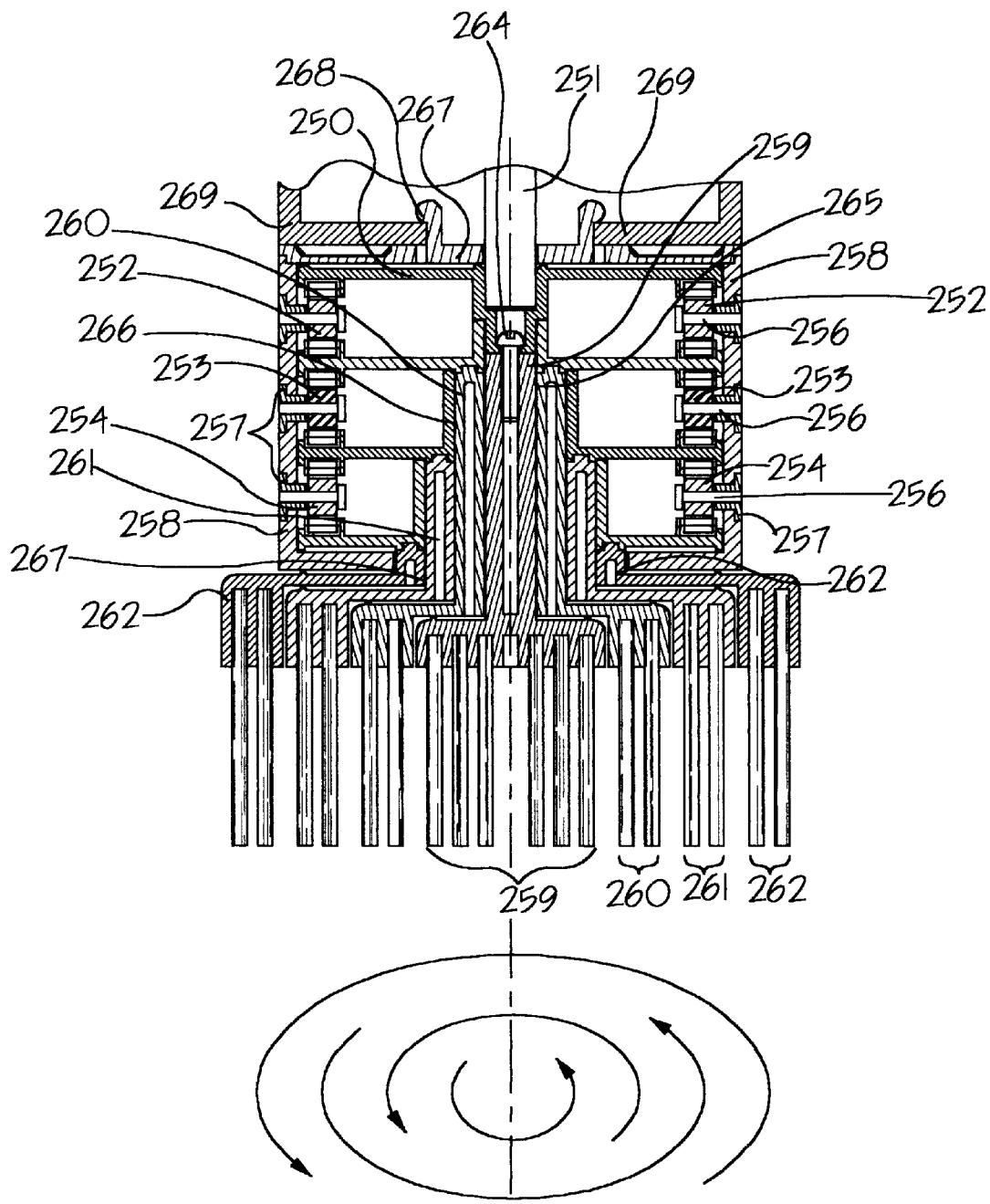
Figures 2, 3, 4:
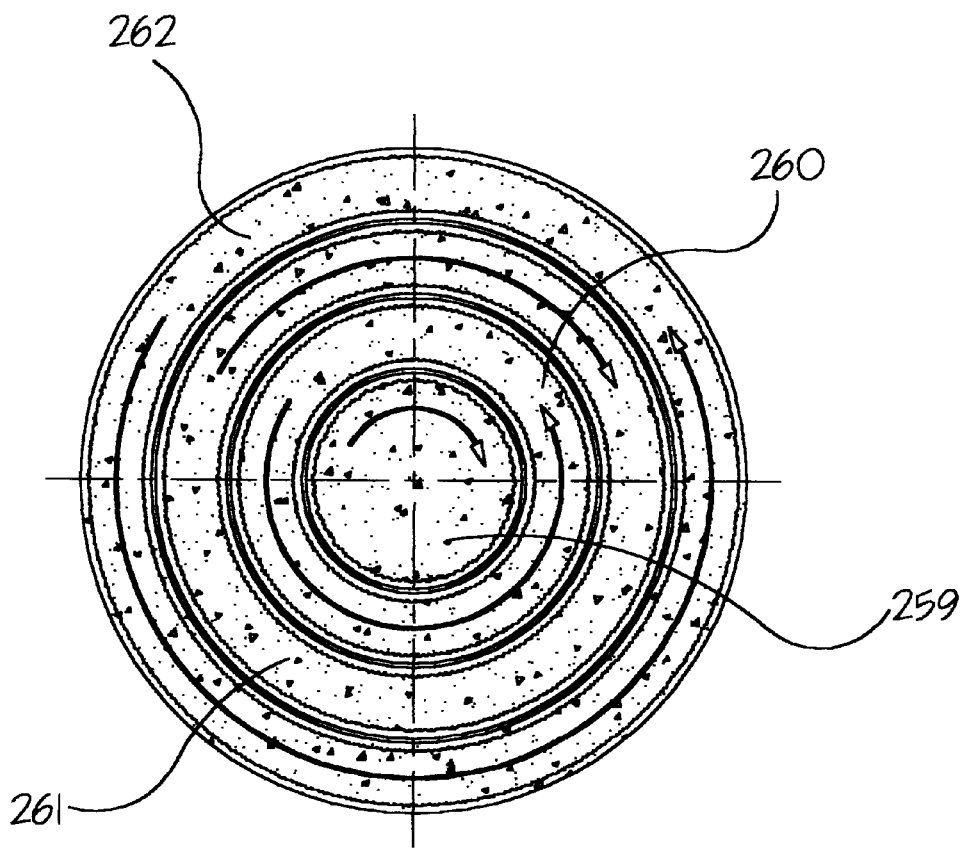
Figure 4:
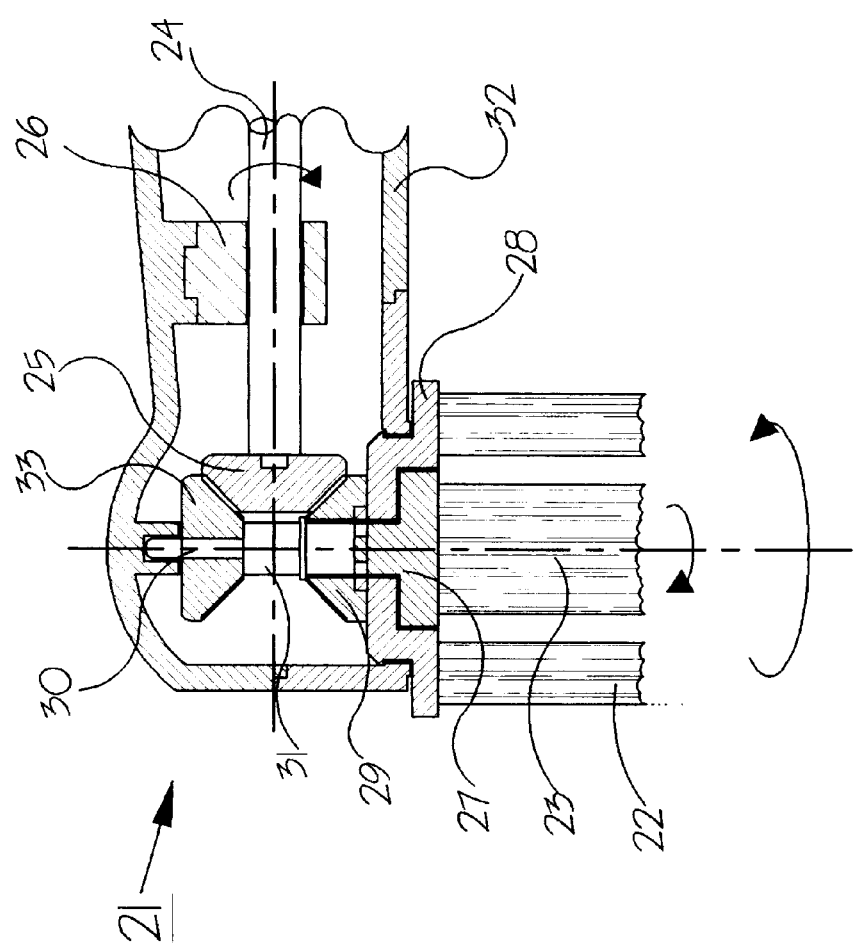
Figure 6:
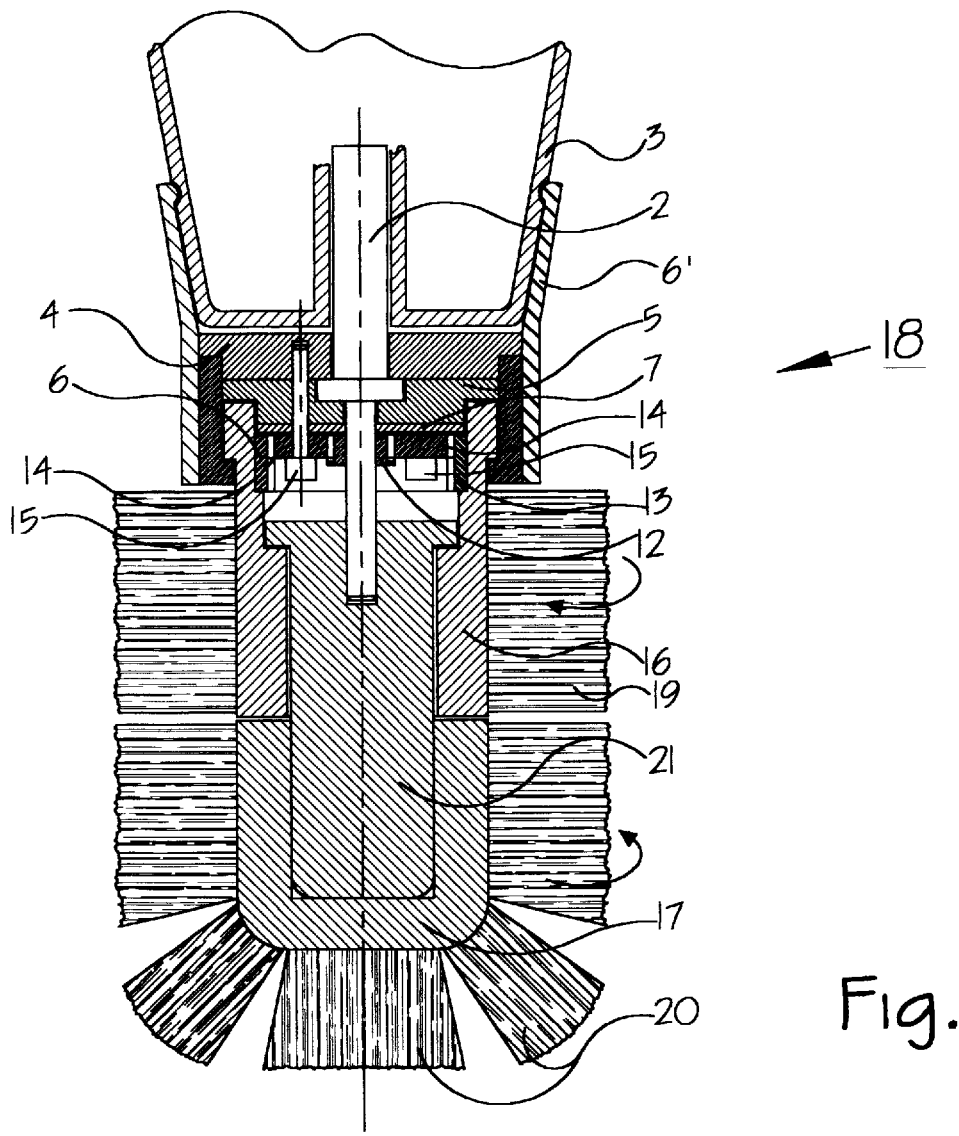

Furthermore, as illustrated in FIG. 6, the respective "inner" and "outer" bristle support members 16,17 of a cleaning brush 18, which may otherwise correspond to the one shown in FIGS. 2 and 3, need not necessarily be concentrically arranged, but rather may be arranged in a three dimensional configuration to provide axially spaced but still coaxially rotatable bristle assemblies 19 and 20. As illustrated, the gear arrangement of this example may be identical to that shown in FIGS. 2 and 3, with the only difference being that the bristle support members are extended in a cylindrical configuration, although other gear arrangements could of course also be used with this offset configuration, including the gear arrangement shown in FIG. 2-1.

In a further variation of the structure shown in FIGS. 2 and 3, as illustrated in FIG. 4, the cleaning brush is in the form of a toothbrush 21 having an outer bristle assembly 22 which rotates in a first direction and an inner bristle assembly 23 which rotates in a second direction. Because the toothbrush 21 must be perpendicular to the drive shaft 24, a different gear arrangement is used. In this variation, a bevel drive gear 25, or similar gear such as a crown gear, is connected to the drive shaft. The motor (not shown) and drive shaft 24 may be of an identical construction to conventional rotary toothbrushes, including appropriate bearing supports 26 in a housing 32. The bristle assemblies of the toothbrush are supported by concentric inner and outer support members 27 and 28, the outer support member 28 being connected directly to a second bevel gear 29 or similar gear such as a crown gear, and the inner support member 27 being connected via a second shaft 30 to a third bevel gear 33 or similar type of gear positioned such that both of gears 29 and 33 engage the drive gear 25 and rotate in response thereto to drive the inner and outer bristle supporting members 27 and 28 in opposite directions.

As a result of this improved electric toothbrush structure which employs the principles of the first preferred embodiment of the invention, a more stable brush action, more intense cross cleaning, and a generally better cleaning effect relative to conventional electric toothbrush designs is achieved. In addition, it is anticipated that an even more effective cleaning effect can be obtained achieved by periodically reversing the direction of shaft rotation, for example, by including a flip flop in the motor control circuit.

In a variation of the toothbrush design shown in FIG. 5, a third non-rotatable bristle assembly or ring 35 depending from a housing 38 is added to the first and second bristle assemblies 36 and 37 of an electric toothbrush 34. Those skilled in the art will recognize that this structure is still in accordance with the general concept described in connection with FIG. 1, except that for this example, n=3, $v_1$=+ve, $v_2$=−ve, and $v_3$=0. The stationary outer ring has the advantage of providing a more gentle massaging effect for the gums and to reduce splashing from the inner bristles.

In another variation of the toothbrush design shown in FIG. 5, the gear arrangement of FIG. 5 is replaced by a drive gear 170 connected to shaft 171 and rotatable therewith, as shown in FIGS. 5-1 and 5-3, drive gear 170 in turn engaging a first ring gear 172 and a second gear 173, which as a result are driven by gear 170 to rotate in opposite directions. In this embodiment, first ring gear 172 is connected by means of, for example, a snap fitting 172A to an inner brush assembly 174 which thereby rotates in the direction of rotation of the first ring gear, and the second ring gear 173 is constructed to be integral with the outer brush assembly 175, thereby causing the bristles of the respective inner and outer brush assemblies to rotate in opposite directions to provide improved balance, counter-torque, and cross-cleaning effects. As in the first toothbrush embodiment, it will be appreciated by those skilled in the art that the toothbrush body 176 will include appropriate bearing surfaces for the various moving components, as well as means for assembling the body and shaft to a motor unit.

In yet another variation of the above-described toothbrush embodiments, two of each of elements 172–175 are provided, with the second set of elements 172–175 being indicated in FIGS. 5-2 and 5-4 by reference numerals 172'–175', to form a double head toothbrush. In this variation, power is transmitted from ring gears 172 and 173 to ring gears 172' and 173' by means of an intermediate drive gear 177. Those skilled in the art will appreciate that additional sets of counter-rotating heads could be added to the same drivetrain simply by adding addition intermediate gears corresponding to intermediate gear 177.

Figure 7:
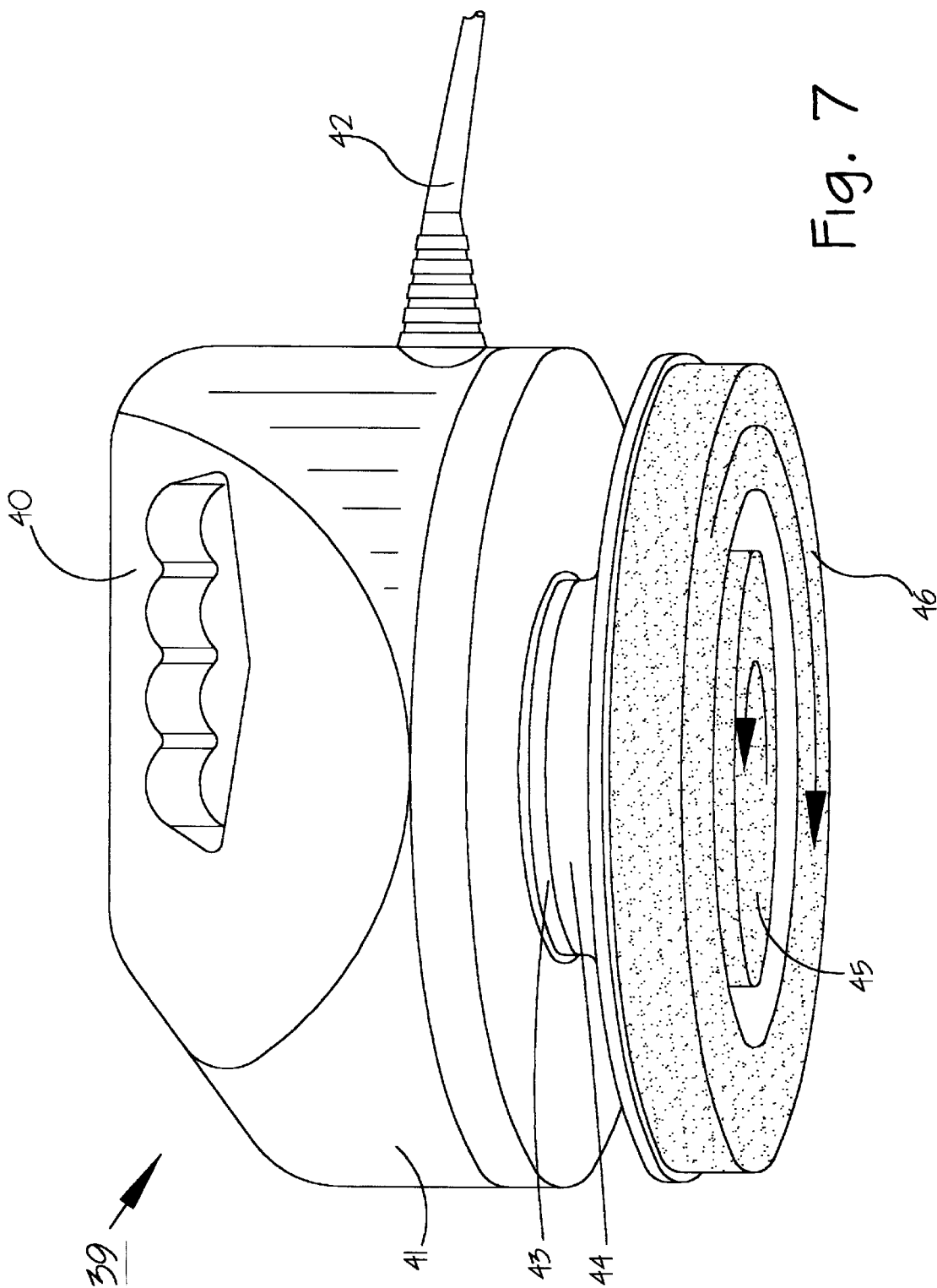
FIG. 7 is a perspective view of a counter-rotating car polisher design constructed in accordance with the principles of the first preferred embodiment of the invention.

FIG. 7 shows an application in which the bristles of the various brush designs are replaced by polishing or buffing discs to obtain a hand-held polisher 39 of the type used to polish automobiles. As discussed above, the problem of balancing forces is especially critical in a car polisher due to the problem of controlling the polisher when the polishing wheel is applied to corners of the automobile. The structure of the transmission mechanism for driving the two oppositely rotating polishing heads using via a common motor and drive shaft may be the same as shown in FIGS. 2 and 4, although variations of the above will undoubtedly occur to those skilled in the art. The illustrated car polisher includes a handle 40 in the housing 41, making it important to minimize the space taken up by the motor and transmission mechanism. Also shown is a power cord 42 for the motor. As illustrated, members 43 and 44 correspond respectively to bearing members 4 and 7 shown in FIG. 2, with the bristle assemblies 23 and 22 shown in FIG. 2 being replace by polishing wheels or discs 45 and 46.

Figure 8:
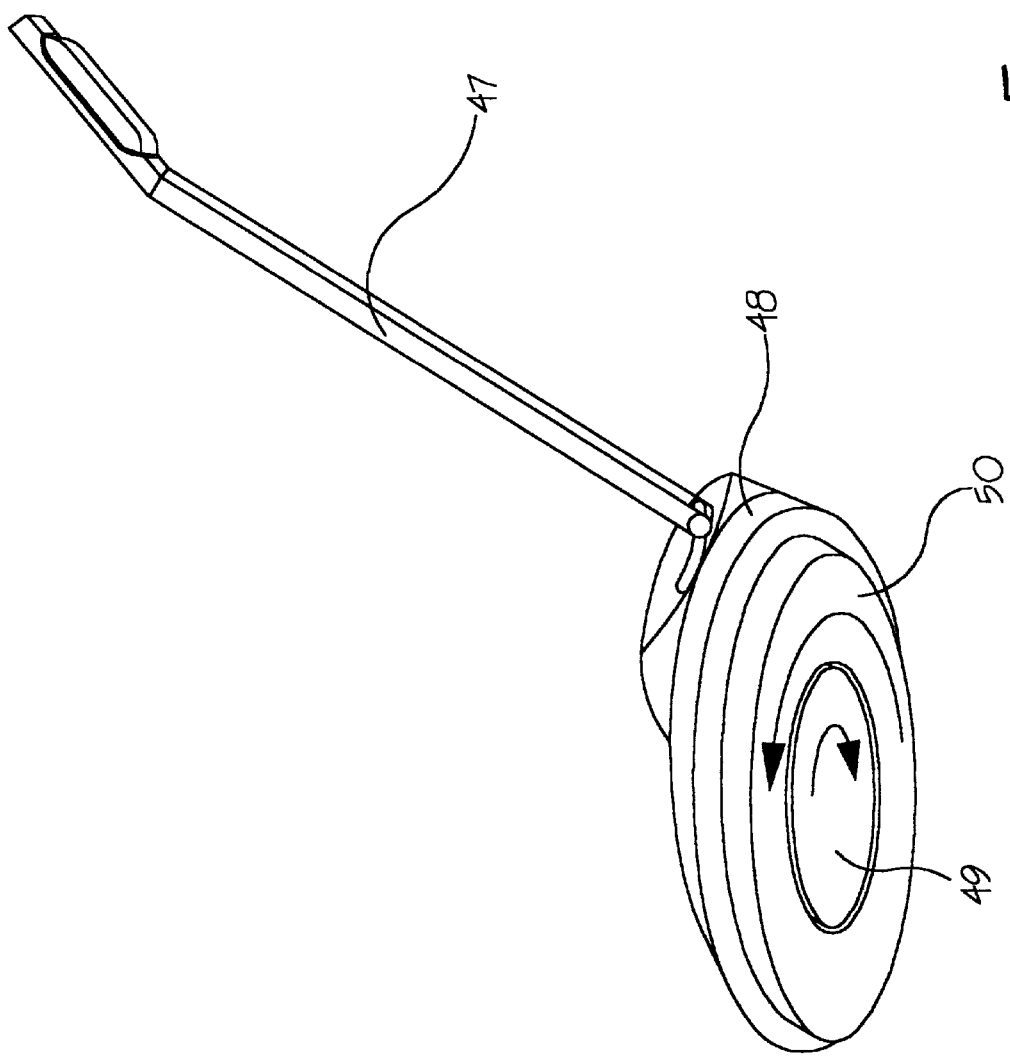
FIG. 8 is a perspective view of a counter-rotating floor polisher design constructed in accordance with the principles of the first preferred embodiment of the invention.

FIG. 8 shows a variation of the polisher illustrated in FIG. 7, in which the basic structure of the first preferred embodiment of the invention is adapted for use as a floor polisher 51 having a pivotable handle 47, main housing 48, and respective counter-rotatable inner and outer polishing discs 49 and 50. Aside from the larger polishing heads and motor, details of this variation of the first preferred embodiment of the invention can be identical to those of the variation shown in FIG. 7.

Figure 9:
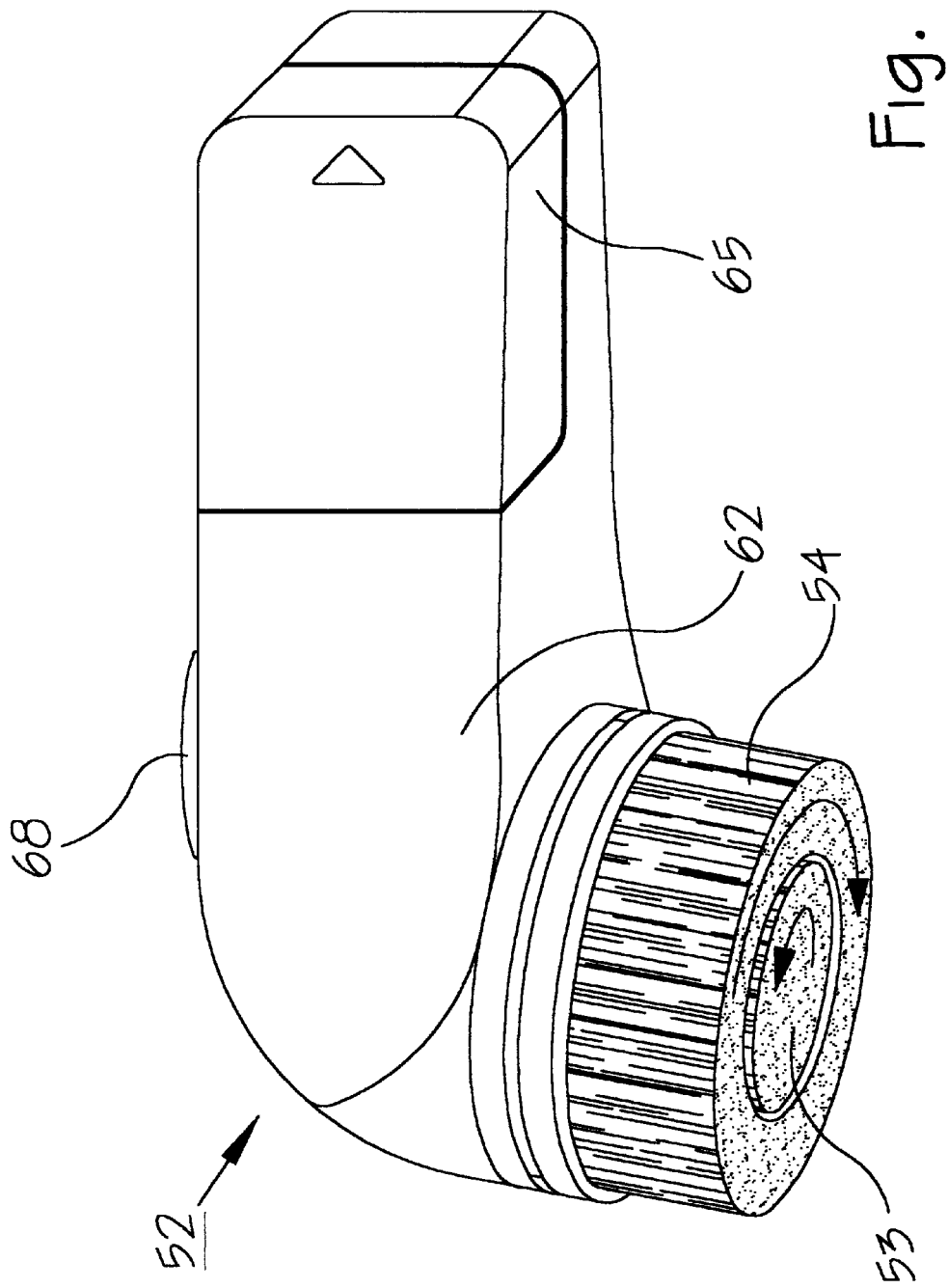
FIG. 9 is a perspective view of a counter-rotating shoe polisher design constructed in accordance with the principles of the first preferred embodiment of the invention.
Figure 10:
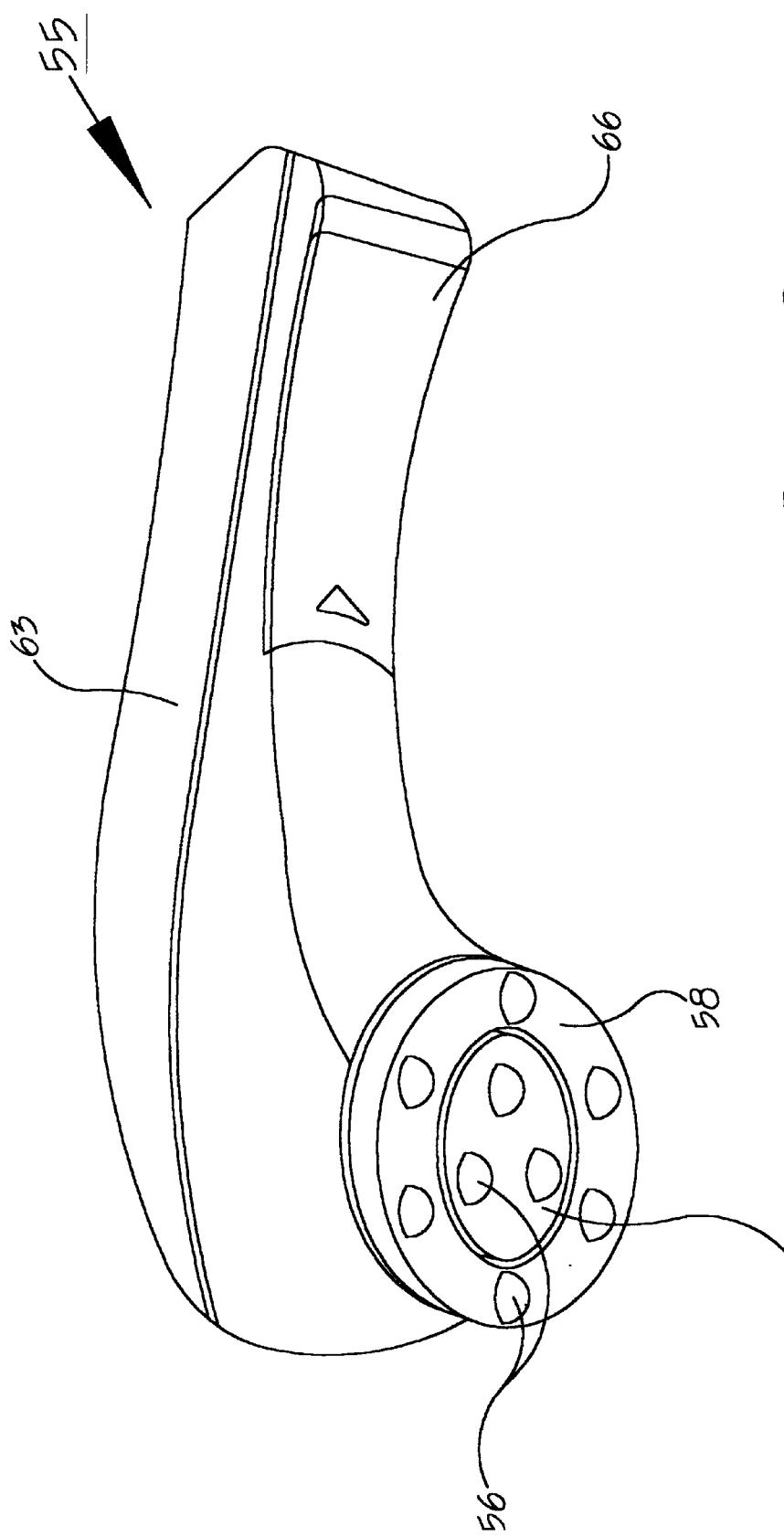
FIG. 10 is a perspective view of a counter-rotating hand-held massager design constructed in accordance with the principles of the first preferred embodiment of the invention.

Finally, FIGS. 9 and 10 show further applications of the principles of the first preferred embodiment of the invention. FIG. 9 shows a hand-held battery operated shoe brush or polisher 52 having oppositely rotating bristle or polishing heads 53 and 54, and FIG. 10 shows a hand-held battery operated massager 55 of the type including a plurality of massaging balls 56 mounted on oppositely rotating heads 57 and 58. The respective housing assemblies 62, 63, and 64 of the respective devices shown in FIGS. 9 and 10, including battery compartment covers 65 and 66, handle 67, and on-off switches or trigger controls 68 and 69 are conventional and therefore need not be further described herein.

FIG. 11 shows the more general situation in which the linear movable members do not oscillate, but rather move continuously. This embodiment is essentially a generalization of the first preferred embodiment of the invention in which the radii are taken to infinity, with side-by-side members n=1 to N being in the form of belts 70 driven by pulleys 71, the pulleys being connected to each other and to a drive shaft 72 by means of gears 73 having different gear ratios in order to achieve different velocities $V_1$ to $V_N$.

Figure 12:
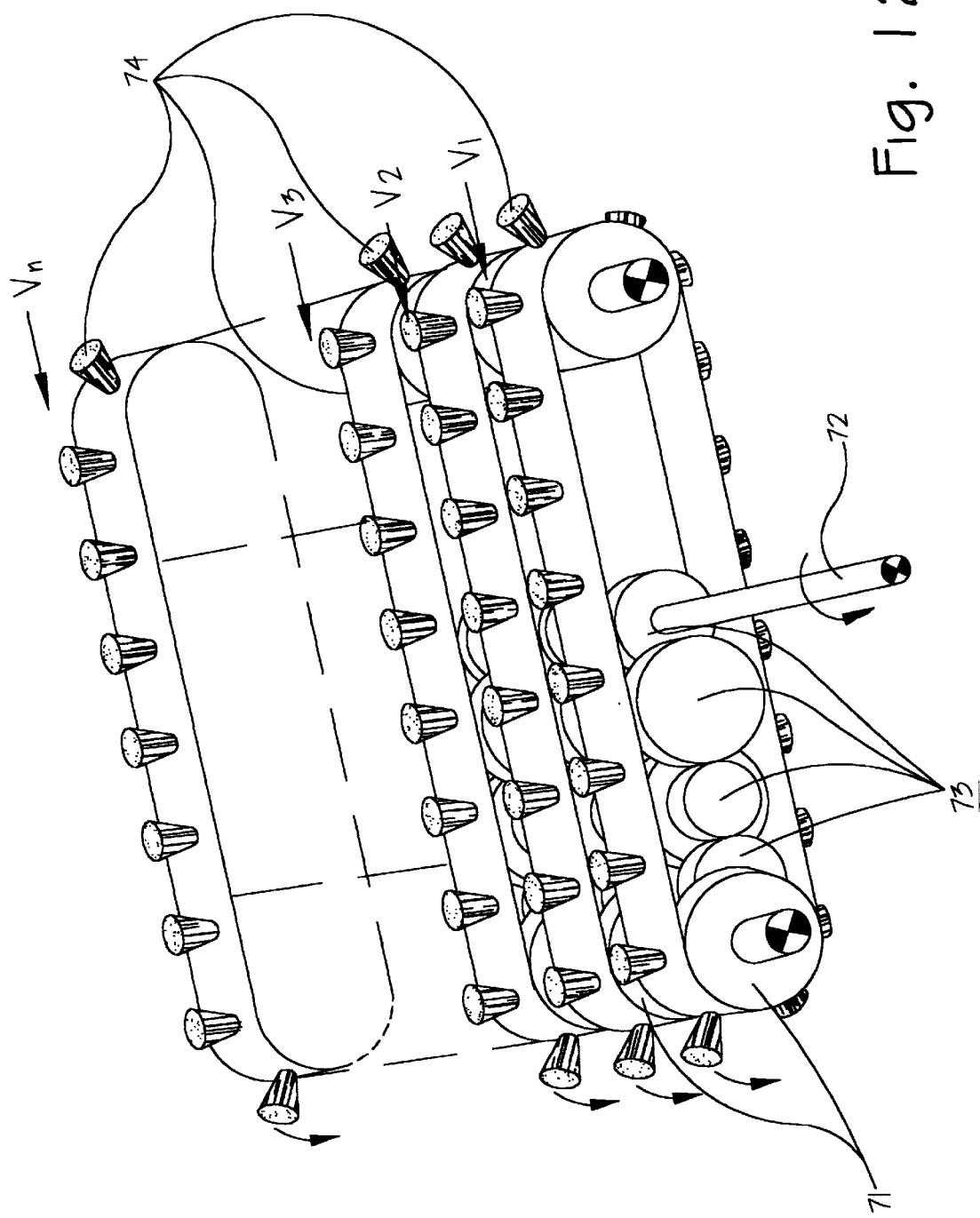
FIG. 12 is a perspective view illustrating an application of the design of FIG. 11 to a brush.
Figure 13:
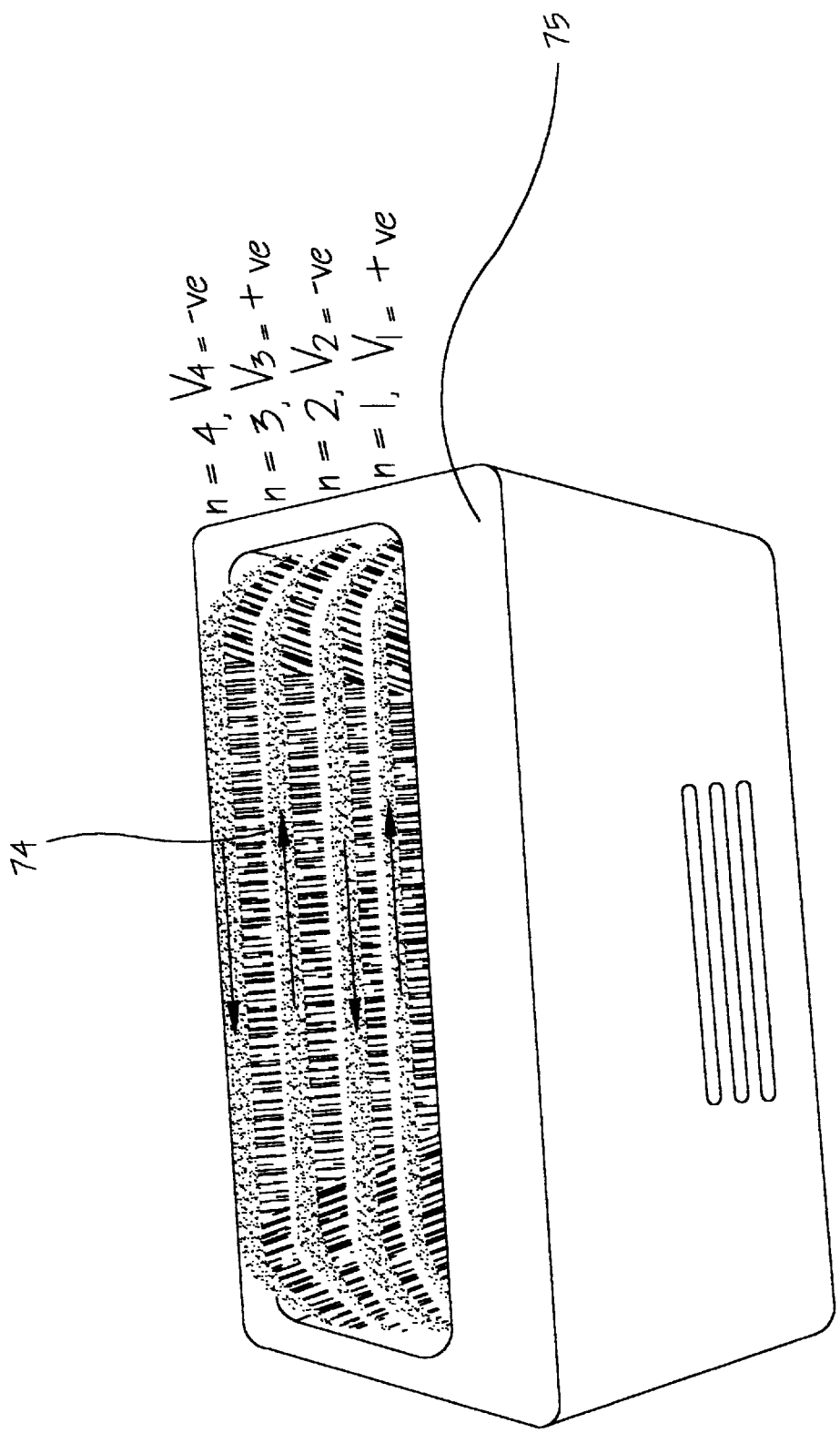
FIG. 13 is a perspective view of a shoe or cleaning brush arranged according to the principles illustrated in FIGS. 11 and 12.
Figure 14:
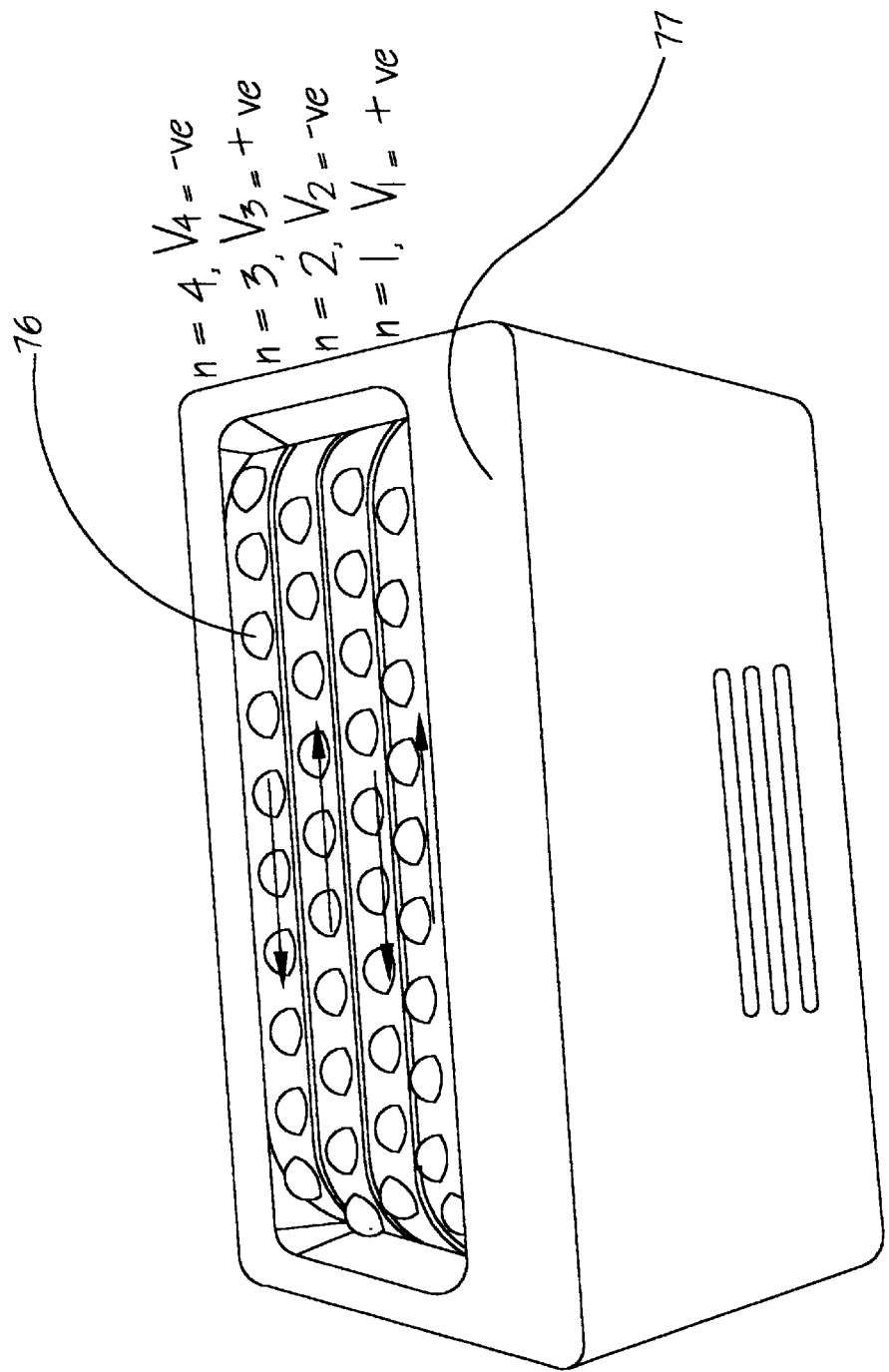
FIG. 14 is a perspective view of massager arranged according to the principles illustrated in FIGS. 11 and 12.

As shown in FIG. 12, for example, the linearly movable members may support bristles 74 of a brush, which may take the form of a shoe or cleaning brush having a housing 75 in which the mechanism of FIG. 12 is mounted, as illustrated in FIG. 13. Similarly, the linearly movable members may support the massaging balls 76 mounted in the housing 77 of a massager, as illustrated in FIG. 14. Those skilled in the art will appreciate that the improved balance and cleaning, brushing, or massaging advantages of the embodiment illustrated in FIGS. 1–10 will also be obtained in the embodiment of FIGS. 11–14 due to the differential motion between the side-by-side tools or heads. In addition, it will be appreciated by those skilled in the art that the mechanism illustrated in FIGS. 11–14 may also be applied to polishers, sanders, and similar household appliances or tools.

In addition to providing for continuous linear motion, as illustrated in FIGS. 11–14, the invention can also take the form of a household appliance or personal grooming device in which the side-by-side tools or heads are caused to reciprocate or oscillate in order to obtain the advantages of improved balance and cleaning effect, as well to reduce the effort needed to manipulate the appliance since the reaction force caused by a tool moving in one direction will be countered by the force of a tool moving in the opposite direction to provide a linear analogue of the counter-torque effect.

For example, as illustrated in FIG. 15, the invention may be embodied by an arrangement 90 for converting the rotation of a shaft 91 into linear oscillations of a plurality of members 92, illustrated as carrying bristles 93 but which may also carry massage massaging balls, sponges, or the like, with each member being 180° out-of-phase in the path of movement relative to a neighboring member. The oscillations are achieved, for example, by a crankshaft 94 to which are pivotally attached a plurality of connecting rods 95, which in turn are pivotally connected to the tools or heads 92 which carry out the function of the apparatus. As was the case with the first preferred embodiment of the invention, it should be appreciated by those skilled in the art that numerous other mechanical arrangements for converting rotational to linear reciprocating motion may be substituted for the illustrated crankshaft arrangement, and that the invention lies not in the use of a crankshaft per se, but in application to a cleaning or personal grooming device, as illustrated in FIGS. 16 and 17.

Figure 16:
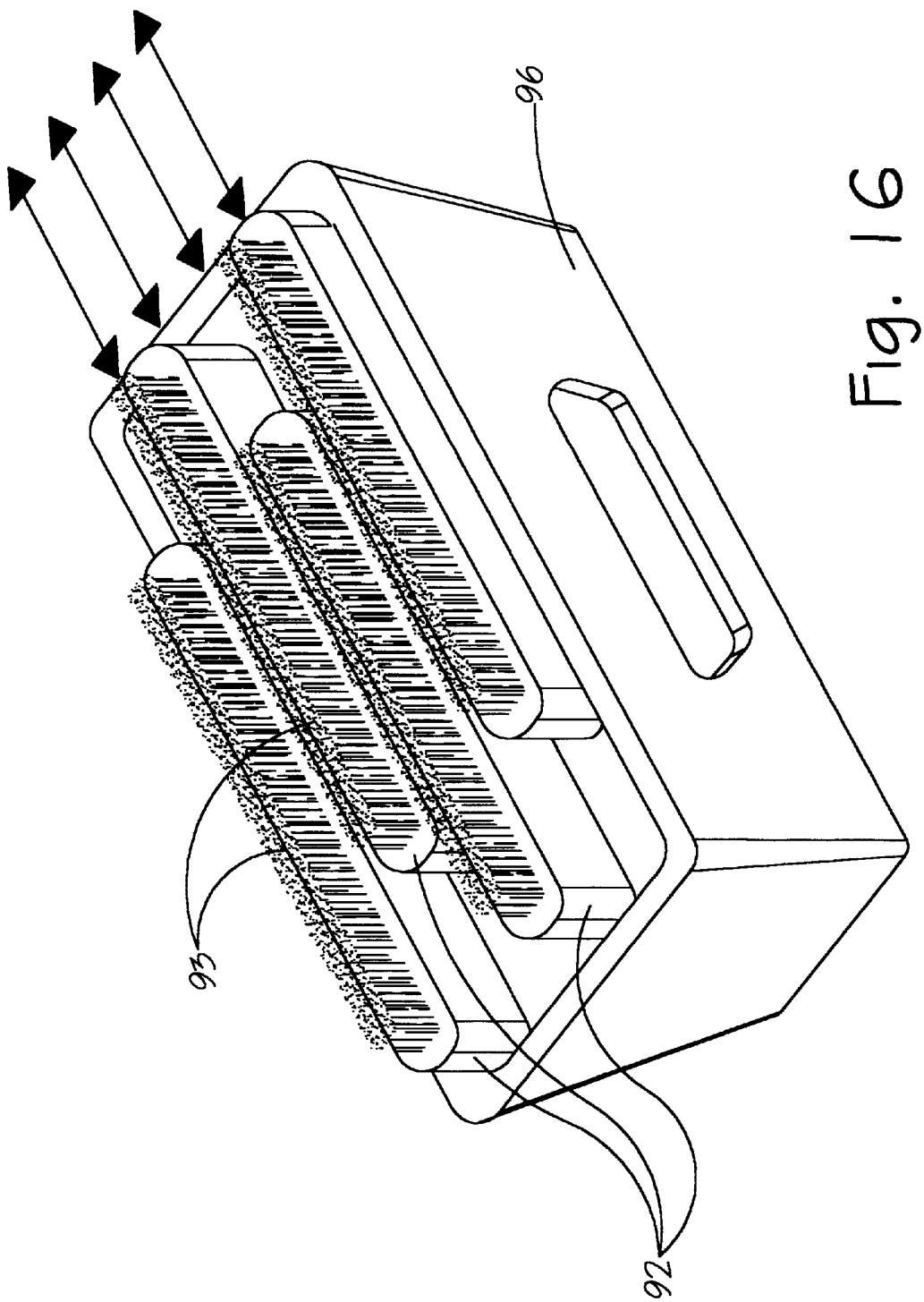
FIG. 16 is a perspective view of a counter-reciprocating shoe brush arranged according to the principles illustrated in FIG. 15.
Figure 17:
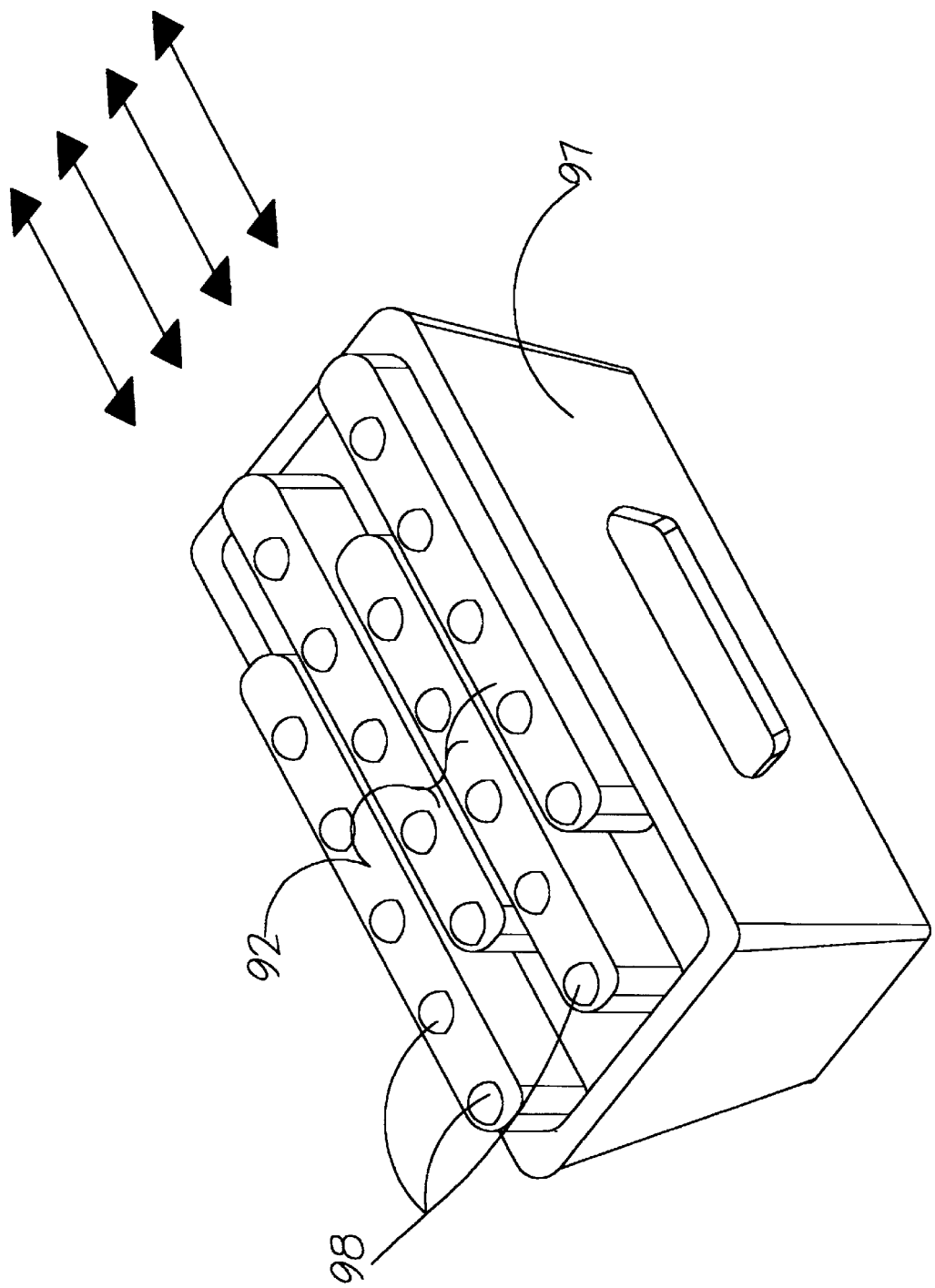
FIG. 17 is a perspective view of a counter-reciprocating massager arranged according to the principles illustrated in FIG. 15.

FIG. 16 shows a cascade-type brush 96 which utilizes the mechanism 90 shown in FIG. 15. The linearly oscillations produced thereby have advantages over the counter-rotating brush in a number of applications. For example, the counter-rotating brush can not be used as a hair brush, head massager, or head washing device of the type intended to simulate human fingers for use during shampooing because the hair will become entangled. The linear oscillating or reciprocating brush with counter oscillations solves this problem. In addition, the linearly-reciprocating brush can be used as a shoe cleaning or polishing device which provides a cross-cleaning effect with minimal vibration due to the canceling moments of inertia. Finally, as shown in FIG. 17, the linear reciprocation principles of this embodiment can be applied to a massager 97, which is similar to the rotary massager shown in FIG. 10 in that it includes a plurality of massaging balls 98 and results in a cross-massaging effect with minimal undesired vibration.

Figure 18:
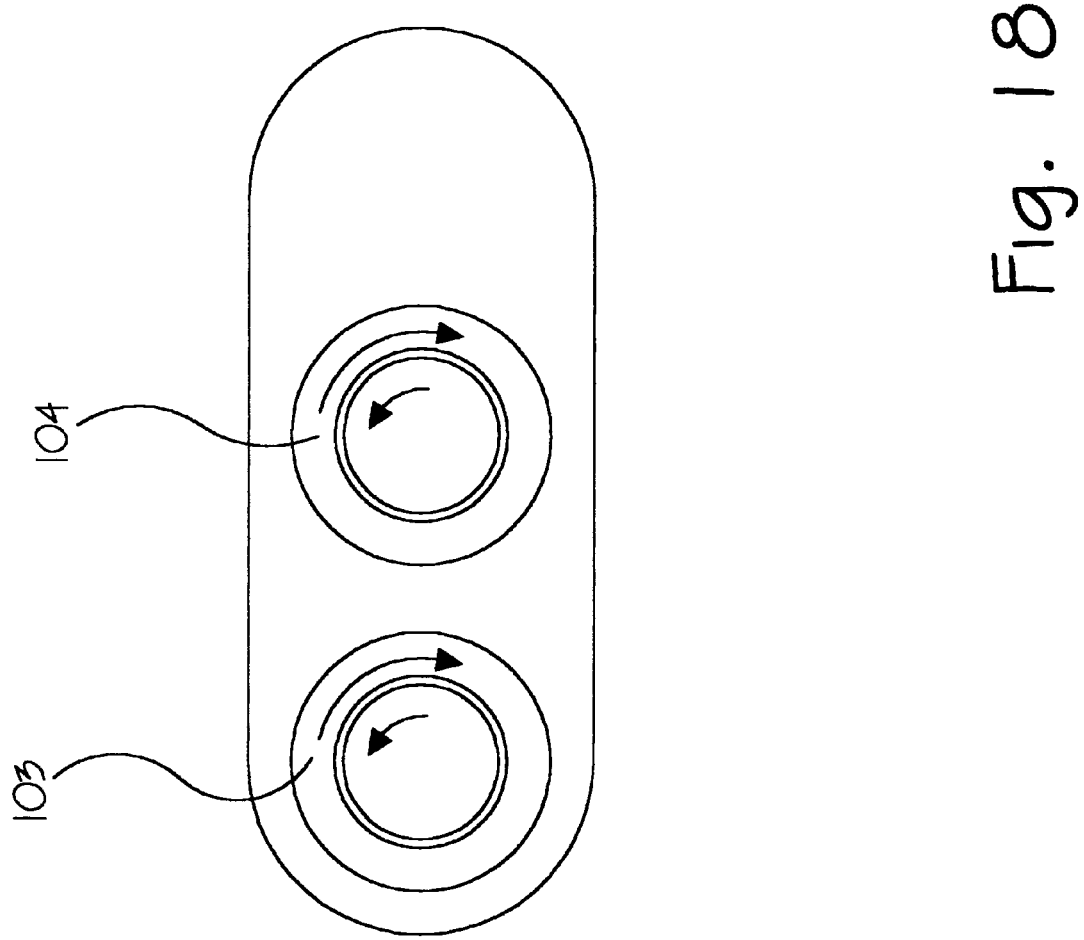
FIG. 18 is a plan view showing a variation of the preferred counter-rotating device having multiple counter-rotation heads.
Figure 19:
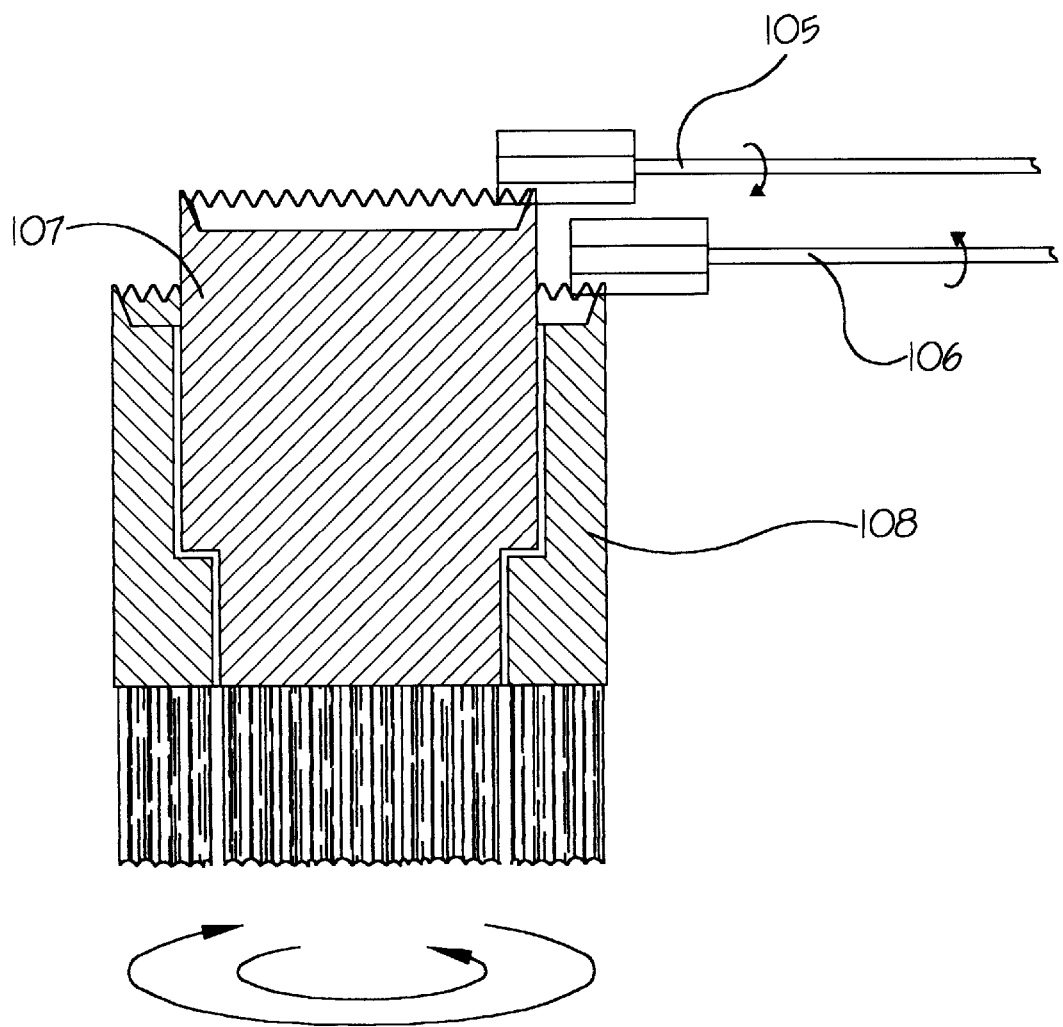
FIG. 19 is a cross-sectional view of a counter-rotating device having multiple drive shafts.

FIG. 18 illustrates a variation of the counter-rotation illustrated in FIGS. 1–10, in which two heads 103 and 104 are provided, the principles of the invention of course being applicable to any desired number of heads, while FIG. 19 illustrates a variation of the mechanisms illustrated in FIGS. 1–10, in which dual shafts 105 and 106 are provided to drive the differentially rotating sections 107 and 108, the principles of the invention being applicable to numerous different shaft and gearing combinations.

Finally, to illustrate a further advantage of the cross-cleaning provided by the invention, FIGS. 20, 20-1, 20-2, and 20-3 depict a fingernail cleaning device in which the two rotating heads 180 and 181 are arranged coaxially, each of the heads being in the form of a cylinder having radially inward facing bristles. This embodiment solves a number of problems which prevent effective cleaning of fingernails by a device having only a single rotation direction. The problems result in part from the shape of a fingernail and in particular the presence of a recess on both sides of the fingernail where it is embedded into the skin. If only a single cylinder were provided and the rotation were in one direction, it would be very difficult and sometimes even impossible to clean both sides of the fingernail in the regions close to the position where the fingernail is embedded into the skin and forms a recess because, as the bristles swipe past the fingernail surface, while the approaching bristle tips can wipe into the recess, the trailing bristles tend to have their shanks slide over the recess with little chance of wiping into the recess. In addition to the problem of inadequate wiping by the trailing bristles, devices having only a single rotating direction have the disadvantages that fingernail polish removed from the front portion tends to be pressed into the trailing recess, causing the polish to accumulate in the trailing recess, and that, because of variations in the shapes of individual fingers, the approaching and trailing contact geometry between the nail and the bristles is different, which may cause one edge to be cleaned less than the other. To overcome these problems, the counter-rotating brushes of this embodiment allow first one edge and then the other to be completely cleaned as the finger is pushed into the device in the manner illustrated in FIGS. 20-1 and 20-2.

Figure 20:
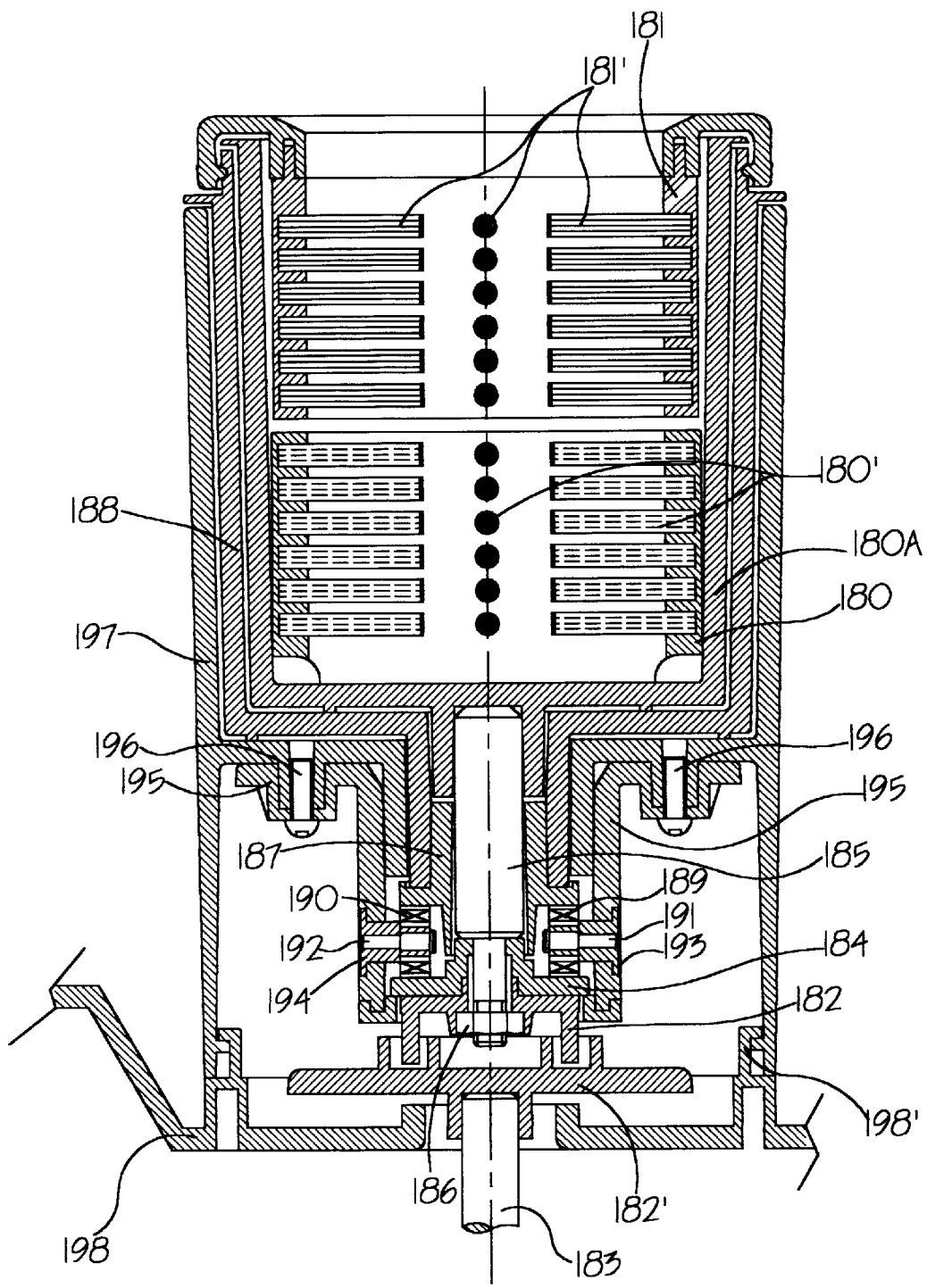
FIG. 20 is a cross-sectional view of a fingernail cleaner which illustrates further principles of the invention.
Figures 1, 20:
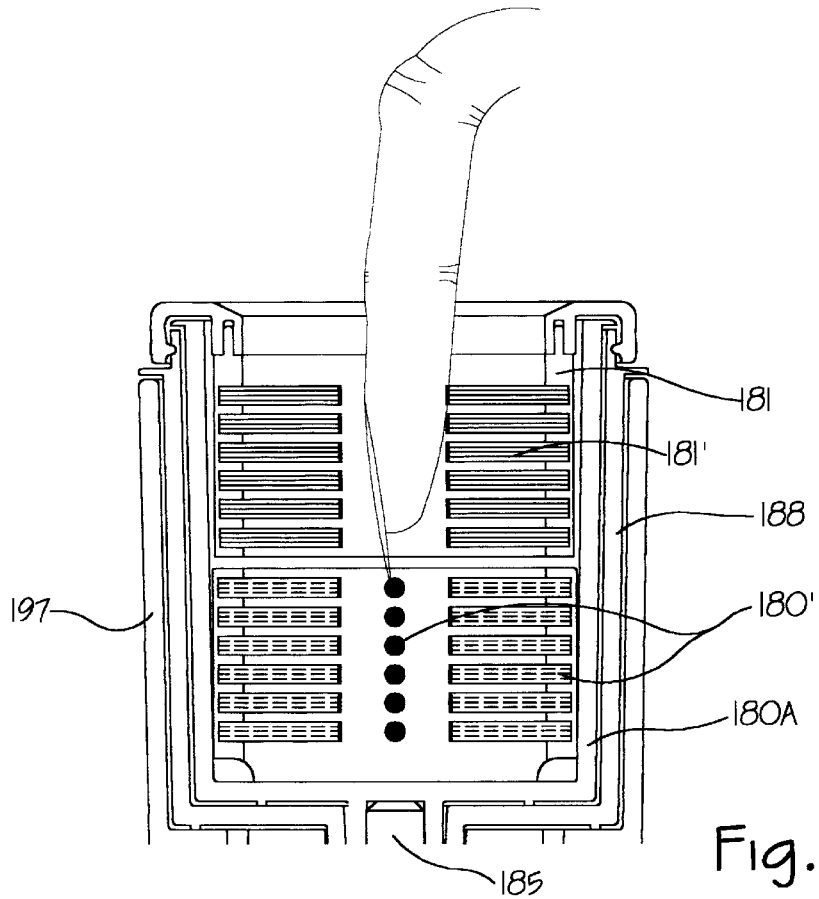
Figures 2, 20:
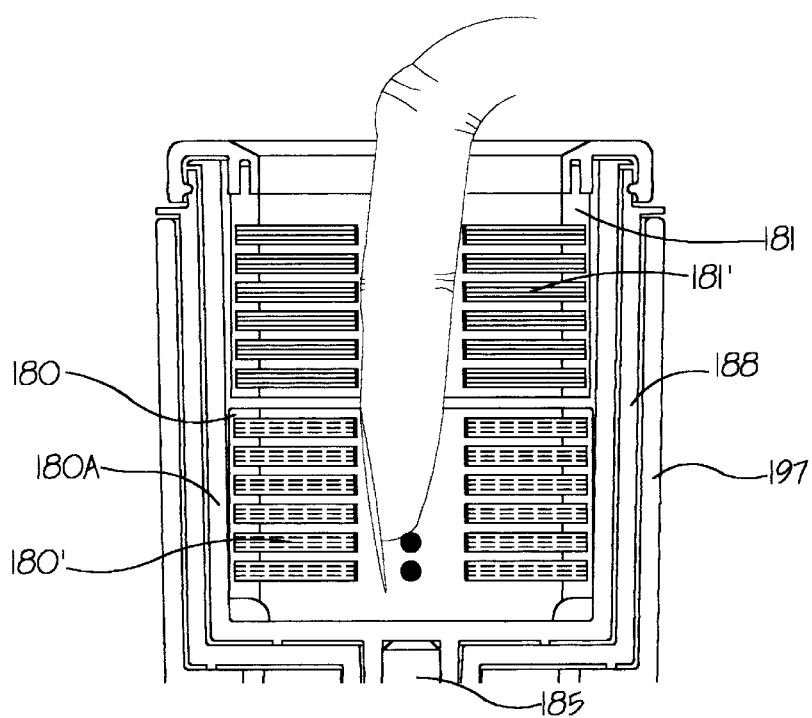
Figures 3, 20:
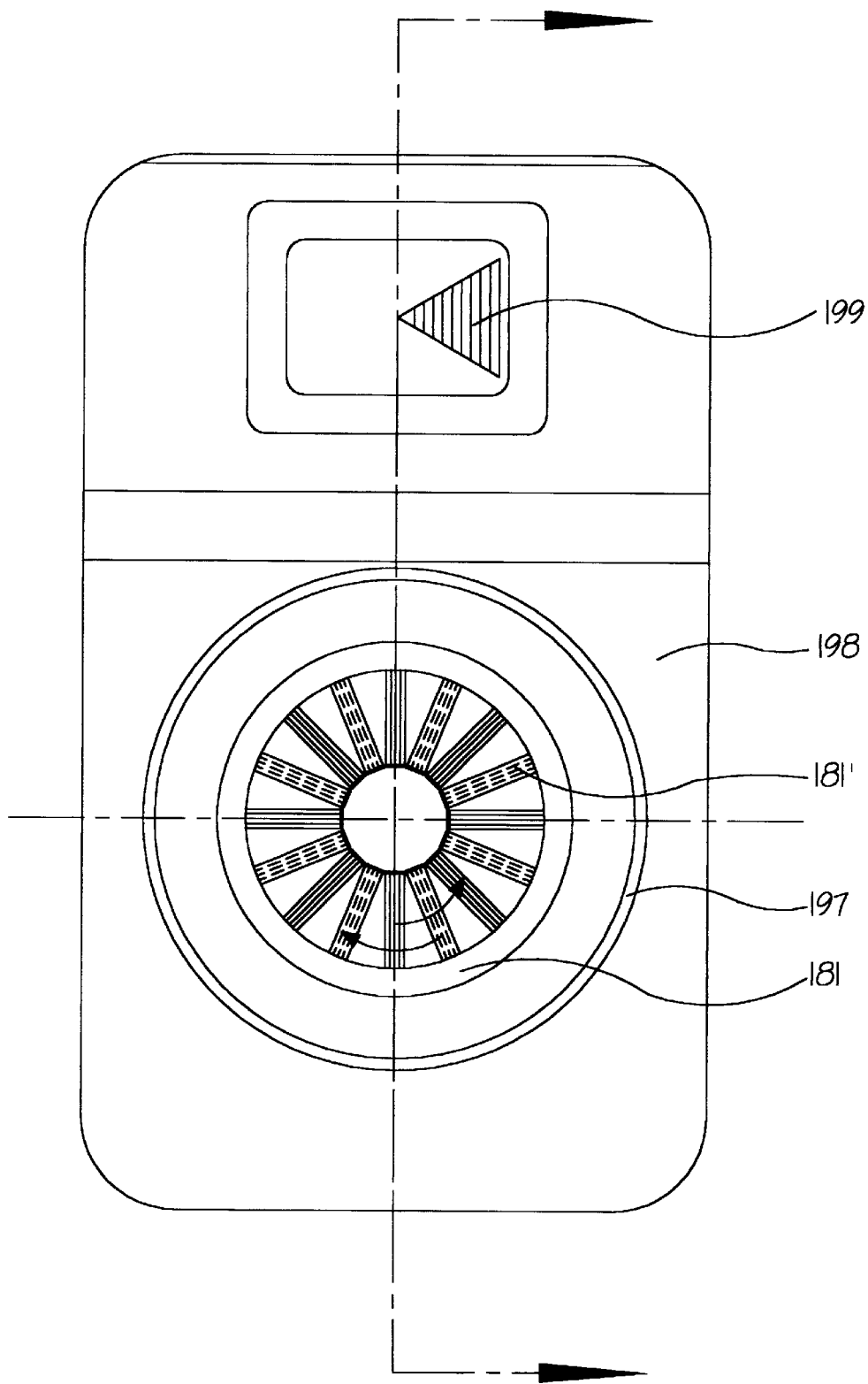

As illustrated in FIG. 20, the rotating heads 180 and 181 of this embodiment may be driven by a gear arrangement similar to that of FIG. 2-1, but the shaft arrangement differs in this device in that a detachable coupling made up of engaging coupling elements 182 and 182' is included to permit the rotating head section to be detached from a main drive unit for cleaning. Coupling element 182' is fixed to a main drive shaft 183 to rotate therewith, and is further coupled to the first ring gear 184 and to an intermediate shaft 185 by a locking nut 186. Intermediate shaft 185 is in turn fixed to rotating head 180 via separate inner cylinder 180A while the second ring gear 187 is fixed to an outer cylinder 188 which in turn is fixed to second rotating head 181, the second ring gear being driven to rotate in a direction opposite that of the first gear by pinions 189,190 engaged with both ring gears and rotatable about pins 191,192 supported by bushings 193,194 in support member 195, which is attached by locking screws 196 to outer casing 197.

As is apparent from FIG. 20, casing 197 can be made separable from the main unit 198, for example by means of a twist off coupling 198', and both of the rotating heads 180 and 181 can be separately removed for cleaning or replacement by first detaching head 181 from cylinder 188 and then detaching head 180 from cylinder 180A. The main unit 198, best illustrated in FIG. 20-3, includes the motor, additional gearing (not shown), and an on/off switch 199.

Figure 22:
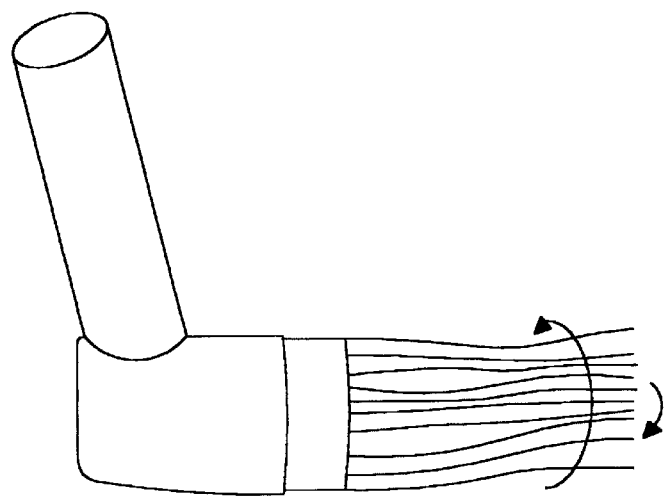
FIG. 22 is a perspective view illustrating the effect of counter-rotation on the type of brush shown in FIG. 21.
Figure 21:
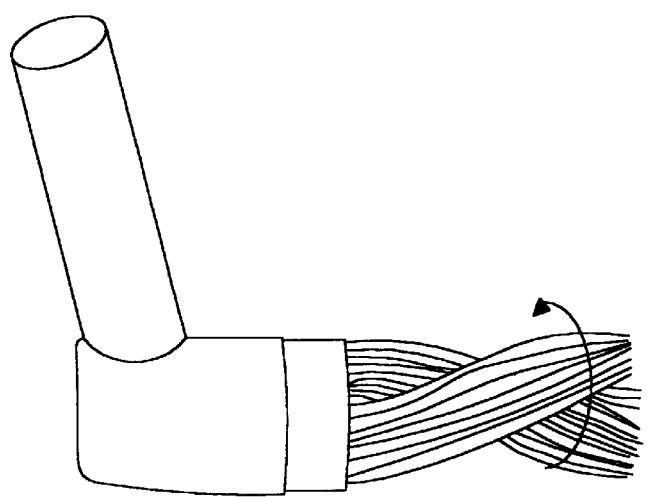
FIG. 21 is a perspective view illustrating the effect of twisting in the case of brushes having relatively long bristle.

FIGS. 21 and 22 are intended to illustrate the effect of eliminating twisting of brushes having relatively long bristles. FIG. 21 shows a single head brush in which the bristles twist as the head is rotated, while FIG. 23 shows a counter-rotating head device according to any of the above embodiments in which twisting is minimized due to the effect of the counter-rotation.

Those skilled in the art will appreciate that numerous analogous cleaning devices, such as electric toothbrushes, can also use the linear differential motion or linear oscillation motion principles of the invention, and that the differential rotation principles of the invention can also be generalized to a variety of different head or tool configurations, and to appliances other than the ones illustrated herein. For example, FIG. 18 shows a variation of the counter-rotation mechanism illustrated in FIGS. 1–10, in which two heads are provided, the principles of the invention being applicable to any desired number of heads, while FIG. 19 illustrates a variation of the mechanisms illustrated in FIGS. 1–10, in which dual shafts 105 and 106 are provided to drive the differentially rotating sections 107 and 108, the principles of the invention being applicable to numerous different shaft and gearing combinations. Consequently, it is intended that the invention not be limited to the specific embodiments illustrated in the drawings and accompanying description set forth above, except as necessary in view of the prior art, and that the invention instead be limited solely by the appended claims.

I claim:

1. A household appliance including a rotating head divided into a number n of coaxially rotatable members having respective contact areas for contacting a surface, where n is an integer greater than 1 and further comprising means for driving at least two of said n members at mutually different velocities, said velocities and contact areas of said coaxially rotatable members being selected such that a sum of torques resulting from rotation of said members in a first direction approximately equals a sum of torques resulting from rotation of said members in a second direction opposite the first direction when said heads contact said surface to balance said appliance and thereby minimize an effort needed to utilize the device.

2. A household appliance as claimed in claim 1, wherein the number n is 2, and said two members are concentrically arranged to rotate in opposite directions.

3. A household appliance as claimed in claim 2, wherein said means for driving said n members comprises a ring gear, a rotating shaft, a motor, an appliance housing, at least one idler gear, and a drive gear, wherein an outer one of said two concentrically arranged members is affixed to the ring gear, wherein an inner one of said two concentrically arranged members is driven directly by the rotating shaft, wherein the rotating shaft is driven by the motor, wherein the ring gear is driven by the at least one idler gear, said idler gear being fixed with respect to the housing, and wherein the drive gear is attached to and rotatable with the rotating shaft.

4. A household appliance as claimed in claim 2, wherein an inner one of said two concentrically arranged members is affixed to a first ring gear, wherein an outer one of said two concentrically arranged members is affixed to a second ring gear, and wherein the two ring gears are driven by at least one pinion in engagement with both ring gears, said pinion being connected to and driven by a motor driven shaft.

5. A household appliance as claimed in claim 2, wherein an outer one of said two concentrically arranged members is affixed to a first ring gear, wherein an inner one of said two concentrically arranged members is affixed to a second ring gear, and wherein the first ring gear is driven by a motor-driven shaft, the first ring gear causes at least one pinion to rotate, and rotation of the pinion causes the second ring gear to rotate in a direction opposite to the direction of rotation of the first ring gear and at an angular speed equal to an angular speed of the first ring gear an axis of rotation of the pinion being perpendicular to axes of rotation of the first and second ring gears.

6. A household appliance as claimed in claim 5, further comprising at least one additional pair of concentrically arranged members, at least one additional pair of ring gears for driving said additional pair of concentrically arranged members, and an intermediate gear for transmitting power from said first and second ring gears to said additional pair of ring gears.

7. A household appliance as claimed in claim 2, wherein each of said concentrically arranged members carries a polishing head.

8. A household appliance as claimed in claim 2, wherein each of said concentrically arranged members carries massaging balls.

9. A household appliance as claimed in claim 2, wherein each of said concentrically arranged members carries bristles having a length which would cause twisting of the bristles in the absence of counter-rotation.

10. A household appliance as claimed in claim 1, wherein said n members are concentrically arranged and each of said concentrically arranged members carries a plurality of bristles to form a counter-rotating brush, wherein said means for driving said n members drives at least two of said n members in opposite directions so as to provide a cross-cleaning effect between said at least two of said n members.

11. A household appliance as claimed in claim 10, wherein n equals two, and said means for driving said n members comprises a ring gear, a rotating shaft, a motor, an appliance housing, at least one idler gear, and a drive gear, wherein an outer one of said two concentrically arranged members is affixed to the ring gear, wherein an inner one of said two concentrically arranged members is driven directly by the rotating shaft, wherein the rotating shaft is driven by the motor, wherein the ring gear is driven by the at least one idler gear, said idler gear being fixed with respect to the housing, and wherein the drive gear is attached to and rotatable with the rotating shaft.

12. A household appliance as claimed in claim 10, wherein an outer one of said two concentrically arranged members is affixed to a first ring gear, wherein an inner one of said two concentrically arranged members is affixed to a second ring gear, and wherein the first ring gear is driven by a motor-driven shaft, the first ring gear causes at least one pinion to rotate, and rotation of the pinion causes the second ring gear to rotate in a direction opposite to the direction of rotation of the first ring gear and at an angular speed equal to an angular speed of the first ring gear, an axis of rotation of the pinion being perpendicular to axes of rotation of the first and second ring gears.

13. A household appliance as claimed in claim 12, further comprising a sleeve having latch arms arranged to be inserted into and engage a central opening in a main housing that contains said motor and gear trains arranged to drive said shaft, thereby securing said rings to said housing as the shaft is inserted into a bushing provided in the first ring gear.

14. A household appliance as claimed in claim 10, wherein said brush is an electric toothbrush.

15. A household appliance as claimed in claim 14, wherein said means for driving said n members comprises a first gear attached to a first of said at least two of said n members, a second gear attached to a second of said at least two of said n members, and a third gear for driving said first and second gears in opposite directions, said third gear being rotatable about an axis perpendicular to a common axis of rotation of said first and second gears.

16. A household appliance as claimed in claim 14, wherein said means for driving said n members comprises a first ring gear attached to a first of said at least two of said n members, a second ring gear attached to a second of said at least two of said n members, and a third gear for driving said first and second ring gears in opposite directions, said third gear being rotatable about an axis perpendicular to a common axis of rotation of said first and second ring gears.

17. A household appliance as claimed in claim 1, wherein said members are axially spaced but coaxially rotatable bristle supporting members.

18. A household appliance as claimed in claim 17, wherein said bristle supporting members are arranged to clean fingernails.

19. A household appliance as claimed in claim 18, wherein each of said bristle-supporting members is in the form of a cylinder having radially inward facing bristles.

20. A household appliance as claimed in claim 19, wherein a first of said two sleeves is affixed to a first ring gear drive by said motor, wherein a second of said two sleeves is affixed to a second ring gear, and further comprising at least one pinion in engagement with both ring gears, said pinion transmitting power from said first ring gear to said second ring gear, whereby said two ring gears rotate in opposite directions and at a same speed.

21. A household appliance as claimed in claim 20, wherein said first ring gear is connected to the motor via a detachable coupling arranged to permit said sleeves to be detached from a main motor-housing drive unit for cleaning.

22. A household appliance as claimed in claim 17, wherein at least one of said bristle supporting members is in the form of a cylinder having radially outward facing bristles.

23. A household appliance as claimed in claim 1, wherein the number n of said members is 3.

24. A household appliance as claimed in claim 23, wherein two of said three members are oppositely rotatable, and wherein the third of said three members is stationary.

25. A household appliance as claimed in claim 24, wherein said members are arranged to support bristles of an electric toothbrush.

26. A household appliance as claimed in claim 1, wherein said appliance is a handheld electric mixer.

27. A household appliance as claimed in claim 1, further comprising a module and a main housing, and wherein said two mutually differentially driven members are supported by said module, being detachable from said main housing.

28. A household appliance including a rotating head divided into n coaxially rotatable members having respective contact areas for contacting a surface, and further comprising means for driving at least two of said n members at mutually different velocities, said velocities and contact areas of said coaxially rotatable members being selected that a sum of torques resulting from rotation of said members in a first direction approximately equals a sum of torques resulting from rotation of said members in a second direction opposite the first direction when said heads contact said surface to balance said appliance and thereby minimize an effort needed to utilize the device, wherein said n members are concentrically arranged and each of said concentrically arranged members carries a plurality of bristles to form a counter-rotating electric toothbrush, wherein said means for driving said n members drive at least two of said n members in opposite directions so as to provide a cross-cleaning effect between said at least two of said n members, wherein said means for driving said n members comprises a first ring gear attached to a first of said at least two of said n members, a second ring gear attached to a second of said at least two of said n members, and a third gear for driving said first and second ring gears in opposite directions, said third gear being rotatable about an axis perpendicular to a common axis of rotation of said first and second ring gears, and further comprising third and fourth members each having bristles attached thereto and coaxially rotatable about a second axis parallel to an axis of rotation of said first and second of said at least two of said n members, said third and fourth members being respectively attached to fourth and fifth gears, said fourth and fifth gears being ring gears coaxially rotatable about said second axis, said fourth and fifth gears being respectively driven in opposite directions by a shaft having at opposite ends sixth and seventh gears and connected by the shaft, said first and second ring gears engaging said sixth gear to thereby transmit power to said sixth gear, said shaft, and said seventh gear, and said seventh gear engaging said fourth and fifth gears to transmit power to said fourth and fifth gears, thereby transferring power from said first and second of said at least two of said n members to said third and fourth members and driving said third and fourth members in opposite directions, whereby said household appliance thereby forms a double headed electric toothbrush with counter-rotating members in each head for optimal cross-cleaning effect.

29. A household appliance including a rotating head divided into a number n of coaxially rotatable members having respective contact areas for contacting a surface, where n is an integer greater than 1, and further comprising means for driving at least two of said n members at mutually different velocities, said velocities and contact areas of said coaxially rotatable members being selected such that a sum of torques resulting from rotation of said members in a first direction approximately equals a sum of torques resulting from rotation of said members in a second direction opposite the first direction to balance said appliance and thereby minimize an effort needed to utilize the device, wherein the number n is 2, said two members are concentrically arranged to rotate in opposite directions an inner one of said two concentrically arranged members is affixed to a first ring gear, an outer one of said two concentrically arranged members is affixed to a second ring gear, and the two ring gears are driven by at least one pinion in engagement with both ring gears, said pinion being connected to and driven by a motor driven shaft, and further comprising at least one additional pair of concentrically arranged members, at least one additional pair of ring gears for driving said additional pair of concentrically arranged members, and an intermediate gear for transmitting power from said first and second ring gears to said additional pair of ring gears.

* * * * *